(12) United States Patent
Almeida et al.

(10) Patent No.: US 10,196,624 B2
(45) Date of Patent: Feb. 5, 2019

(54) ASPARTIC PROTEASES

(71) Applicant: BIOCANT-ASSOCIAÇÃO DE TRANSFERÊNCIA DE TECNOLOGIA, Cantanhede (PT)

(72) Inventors: Carla Sofia Gomes Malaquias de Almeida, Cantanhede (PT); Isaura Isabel Gonçalves Simões, Cantanhede (PT); Carlos José Fialho Costa Faro, Cantanhede (PT)

(73) Assignee: Biocant—Associacao De Transferencia De Tecnologia (PT)

( * ) Notice: Subject to any disclaimer, the term of this patent is extended or adjusted under 35 U.S.C. 154(b) by 247 days.

(21) Appl. No.: 14/777,847

(22) PCT Filed: Mar. 19, 2014

(86) PCT No.: PCT/PT2014/000017
§ 371 (c)(1),
(2) Date: Sep. 17, 2015

(87) PCT Pub. No.: WO2014/148931
PCT Pub. Date: Sep. 25, 2014

(65) Prior Publication Data
US 2016/0083711 A1 Mar. 24, 2016

(30) Foreign Application Priority Data
Mar. 19, 2013 (GB) .................................. 1305025.7

(51) Int. Cl.
*A23C 9/12* (2006.01)
*C12N 9/50* (2006.01)
*A23C 19/04* (2006.01)

(52) U.S. Cl.
CPC .............. *C12N 9/63* (2013.01); *A23C 9/1209* (2013.01); *A23C 19/041* (2013.01); *C12Y 304/23* (2013.01)

(58) Field of Classification Search
CPC combination set(s) only.
See application file for complete search history.

(56) References Cited

U.S. PATENT DOCUMENTS

| 2006/0003435 A1 | 1/2006 | Soares Pais et al. |
| 2011/0104286 A1 | 5/2011 | Soares Pais et al. |
| 2016/0186160 A1 | 6/2016 | de Almeida et al. |

FOREIGN PATENT DOCUMENTS

| WO | WO 2000/75283 A1 | 12/2000 |
| WO | WO 2009/040778 A1 | 4/2009 |
| WO | WO 2014/148932 A2 | 9/2014 |

OTHER PUBLICATIONS

Pimentel et al. (Characterization and expression analysis of the aspartic protease gene family FEBS Journal 274 (2007) 2523-2539 (Year: 2007).*
Bi et al. Plant Cell Physiol. 46(1): 87-98 (2005), "The Rice Nucellin Gene Ortholog OsAsp1 Encodes an Active Aspartic Protease Without a Plant-specific Insert and is Strongly Expressed in Eerly Embryo".
Bryksa et al. The Journal of Biological Chemistry vol. 286, No. 32, pp. 28265-28275, Aug. 12, 2011 "Structure and Mechanism of the Saposin-like Domain of a Plant Aspartic Protease".
Cordeiro et al. Milchwissenschaft 47 (11) 1992, "Milk clotting and proteolytic activities of purified cynarases from Cynara cardunculus—a comparison to chymosin".
Curto Pedro et al. Applied and Environmental Microbiology, American Society for Microbiology, US, vol. 80, No. 1, Jan. 2014, pp. 86-96, "Establishing the yeast *Kluyveromyces lactis* as an expression host for production of the saposin-like domain of the aspartic protease cirsin".
Egas et al. The Journal of Biological Chemistry. vol. 275, No. 49, Issue of Dec. 8, 2000 pp. 38190-38196, "The Saposin-like Domain of the Plant Aspartic Proteinase Precursor Is a Potent Inducer of Vesicle Leakage".
International Search Report and Written Opinion issued in PCT/PT2014/000017 dated Nov. 6, 2014.
International Search Report and Written Opinion issued in PCT/PT2014/000018 dated Nov. 6, 2014.
Lufrano et al. FEBS Journal 279 (Suppl. 1) (2012) 52-576, "Analysis of the expression of plant specific insert (PSI) domain in the nonconventional system Kluveromyces lactis".
Mazorra-Manzano et al. Phythochemistry, Pergamon Press, GB, vol. 69, No. 13, Oct. 2008, pp. 2439-2448, "Expression and characterization of the recombinant aspartic proteinase A1 from *Arabidopsis thaliana*".
Milisavljevic et al. Journal of Plant Physiology, Urban Und Fischer Verlag, DE vol. 165, No. 9, Jun. 16, 2008, pp. 983-990, "Two types of aspartic proteinases from buckwheat seed—Gene structure and expression analysis".
Munoz et al. Peptides 21 (2010) 777-785, "The swaposin-like domain of potato aspartic protease (StAsp—PSI) exerts antimicrobial activity on plant and human pathogens".
Payie et al. Biochem, J. (2003) 372, 671-678, "Construction, expression and characterization of a chimaeric mammalian—plant-aspartic proteinase".
Picon et al. Milchwissenschaft 50 (7) 1995 393-395, "Kinetics of milk coagulation by mixtures of cyprosin and chymosin".
Prasad et al. Protein Expression and Purification Academic Press, San Diego, CA, vol. 72, No. 2, Aug. 2010, pp. 169-174, "Heterologous expression and characterization of recombinant OsCDR1, a rice aspartic proteinase involved in disease resistance".
Ramalho-Santos et al. Eur. J. Biochem. 255, 133-138 (1998), "Identification and proteolytic processing of procardosin A".

(Continued)

*Primary Examiner* — Kagnew H Gebreyesus
(74) *Attorney, Agent, or Firm* — Adsero IP

(57) ABSTRACT

The invention relates to aspartic proteases, and particularly to aspartic proteases for plants. Disclosed are modified plant aspartic proteases, and methods for their manufacture, and uses thereof. Particularly contemplated are the uses of aspartic proteases in clotting milk.

7 Claims, 13 Drawing Sheets

Specification includes a Sequence Listing.

(56) References Cited

OTHER PUBLICATIONS

Sampaio et al. Journal of Bioscience and Bioengineering, Elsevier, Amsterdam, NL, vol. 105, No. 4, Apr. 2008 pp. 305-312, "Production and characterization of recombinant cyposin B in *Saccharomyces cerevisiae* (W303-1A) strain".

Törmäkangas et al. The Plant Cell, vol. 13(9), 2021-2032, Sep. 2001, "A Vacuolar Sorting Domain May Also Influence the Way in Which Proteins Leave the Endoplasmic Reticulum".

White et al. "Processing, activity, and inhibition of recombinant cyprosin, an aspartic proteinase from Cardoon (*Cynara cardunculus*)", Journal of Biological Chemistry, American Society for Biochemistry and Molecular Biology, US, vol. 274, No. 24, Jun. 11, 1999, pp. 16685-16693.

\* cited by examiner

>pCBwoPSI (proCardosin B sequence without the PSI sequence):
>MVSNGGLLRVGLKKRKVDRLDQLRAHGVHMLGNARKDFGFRRTLRDSGSGIVAL
TNDRDTAYYGEIGIGTPPQNFAVIFDTGSSDLWVPSTKCDTSLACVIHPRYDSGDSS
TYKGNGTTASIQYGTGAIVGFYSQDSVEVGDLVVEHQDFIETTEEDDTVFLKSEFDG
ILGLGFQEISAGKAVPVWYNMVNQGLVEEAVFSFWLNRNVDEEEGGELVFGGVDP
NHFRGNHTYVPVTRKGYWQFEMGDVLIGDKSSGFCAGGCAAIADSGTSFFAGPTAI
ITQINQAIGAKGGGGSAESIVDCNGISSMPNIAFTIGSKLFEVTPEQYIYKVGEGEAAT
CISGFTALDIMSPQGPIWILGDMFMGPYHTVFDYGKLRVGFAEAV
[SEQ ID NO: 1]

pCAwoPSI (proCardosin A sequence without the PSI sequence):
MSDDGLIRIGLKKRKVDRIDQLRGRRALMEGNARKDFGFRGTVRDSGSAVVALTND
RDTSYFGEIGIGTPPQKFTVIFDTGSSVLWVPSSKCINSKACRAHSMYESSDSSTYK
ENGTSGAIIYGTGSITGFFSQDSVTIGDLVVKEQDFIEATDEADNVFLHRLFDGILGLS
FQTISVPVWYNMVNQGLVKERRFSFWLNRNVDEEEGGELVFGGLDPNHFRGDHT
YVPVTYQYYWQFGIGDVLIGDKSTGFCAPGCQAFADSGTSLLSGPTAIVTQINHAIG
ANGGGGSEELQVDCNTLSSMPNVSFTIGGKKFGLTPEQYILKVGKGEATQCISGFT
AMDATLLGPLWILGDVFMRPYHTVFDYGNLLVGFAEAA
[SEQ ID NO: 2]

pCA PSI sequence:
VMNQQCKTVVSRYGRDIIEMLRSKIQPDKICSHMKLCTFDGARDVSSIIESVVDKNN
DKSSGGIHDEMCTFCEMAVVWMQNEIKQSETEDNIINYANELCEHLSTS
[SEQ ID NO: 3]

pCB PSI sequence:
VLNQQCKTLVGQYGKNMVQMLTSEVQPDKICSHMKLCTFDGAHDVRSMIESVVDK
NNDKSSGGEICTFCEMALVRMQNEIKRNETEDNIINHVNEVCDQLPTS
[SEQ ID NO: 4]

pCB (proCardosin B sequence):
MVSNGGLLRVGLKKRKVDRLDQLRAHGVHMLGNARKDFGFRRTLRDSGSGIVALT
NDRDTAYYGEIGIGTPPQNFAVIFDTGSSDLWVPSTKCDTSLACVIHPRYDSGDSST
YKGNGTTASIQYGTGAIVGFYSQDSVEVGDLVVEHQDFIETTEEDDTVFLKSEFDGI
LGLGFQEISAGKAVPVWYNMVNQGLVEEAVFSFWLNRNVDEEEGGELVFGGVDP
NHFRGNHTYVPVTRKGYWQFEMGDVLIGDKSSGFCAGGCAAIADSGTSFFAGPTAI
ITQINQAIGAKGVLNQQCKTLVGQYGKNMVQMLTSEVQPDKICSHMKLCTFDGAHD
VRSMIESVVDKNNDKSSGGEICTFCEMALVRMQNEIKRNETEDNIINHVNEVCDQLP
TSSAESMVDCNGISSMPNIAFTIGSKLFEVTPEQYIYKVGEGEAATCISGFTALDIMS
PQGPIWILGDMFMGPYHTVFDYGKLRVGFAEAV
[SEQ ID NO: 5]

Figure 2 pCA (proCardosin A sequence):
MSDDGLIRIGLKKRKVDRIDQLRGRRALMEGNARKDFGFRGTVRDSGSAVVALTND
RDTSYFGEIGIGTPPQKFTVIFDTGSSVLWVPSSKCINSKACRAHSMYESSDSSTYK
ENGTSGAIIYGTGSITGFFSQDSVTIGDLVVKEQDFIEATDEADNVFLHRLFDGILGLS
FQTISVPVWYNMVNQGLVKERRFSFWLNRNVDEEEGGELVFGGLDPNHFRGDHT
YVPVTYQYYWQFGIGDVLIGDKSTGFCAPGCQAFADSGTSLLSGPTAIVTQINHAIG
ANGVMNQQCKTVVSRYGRDIIEMLRSKIQPDKICSHMKLCTFDGARDVSSIIESVVD
KNNDKSSGGIHDEMCTFCEMAVVWMQNEIKQSETEDNIINYANELCEHLSTSSEEL
QVDCNTLSSMPNVSFTIGGKKFGLTPEQYILKVGKGEATQCISGFTAMDATLLGPLW
ILGDVFMRPYHTVFDYGNLLVGFAEAA
    [SEQ ID NO: 6]

pCB-XhoI
*CTCGAGAAAAGAATGGTCTCCAACGGCGGATTGCTTC*
    [SEQ ID NO:7]

pCB-SalI
*GTCGACTCAAACTGCTTCTGCAAATCCCACTCGTAAC*
    [SEQ ID NO:8]

Figure 2 (cont'd)

1: pCBΔPSI
2: pCBΔPSI_4G
3: pCBΔPSI_6G
4: pCBΔPSI_NQG
5: pCBΔPSIΔLinker
6: pCBΔPS_2C
7: pCBΔPSΔLoop
K: non-hydrolyzed κ-casein
C-: non-transformed yeast cells

ASPARTIC PROTEASES

RELATED APPLICATIONS

This application is a 35 U.S.C. § 371 national phase application of PCT/PT2014/000017, filed Mar. 19, 2014 (WO/2014/148931). PCT/PT2014/000017 claims priority to GB Application Serial No. 1305025.7, filed Mar. 19, 2013, which is incorporated herein by reference in its entirety.

FIELD OF THE INVENTION

The present invention relates to aspartic proteases and particularly, although not exclusively, to aspartic proteases from plants.

Incorporated by reference herein in its entirety is the Sequence Listing entitled "Sequence-List.txt", created Oct. 28, 2015, size of 31 kilobytes.

BACKGROUND TO THE INVENTION

Aspartic proteases are peptidases present in animals, plants, fungi and viruses and exhibit a wide range of functions and activities, including: mammalian digestion e.g. chymosin and pepsin A, activation and degradation of polypeptide hormones and growth factors e.g. cathepsin D, regulation of blood pressure e.g. rennin, degradation of haemoglobin by parasites e.g. plasmepsins, proteolytic processing of the HIV polyprotein e.g. retropepsin, involvement in pollen-pistil interactions in plants e.g. Cardosin A.

Aspartic proteases are synthesised as preproenzymes and contain a signal peptide, which is cleaved resulting in a proenzyme which can be secreted and activated autocatalytically. Generally, aspartic proteases consist of a single peptide chain of approximately 320-360 amino acid residues, composed mainly of n-strand structures arranged into two lobes. The catalytic site of the enzyme is located between these two lobes, each containing an aspartate residue which are within hydrogen-bonding distance of each other and act together to activate a water molecule which results in cleavage of the substrate peptide bond (via nucleophilic attack).

Plant aspartic proteases differ from other aspartic proteases in that they comprise a Plant Specific Insert which is cleaved out during protein maturation, besides a signal peptide (responsible for translocation to the ER); a prosegment of 40-50 amino acid residues (involved in the correct folding, stabilisation and sorting of the enzyme); and a mature enzyme possessing two catalytic sequence motifs. The two catalytic aspartate residues in plant aspartic proteases are contained within Asp-Thr-Gly and Asp-Ser-Gly motifs. With a few exceptions, the majority of plant aspartic protease identified so far are synthesized with a preprodomain and subsequently converted to mature two-chain enzymes. Proteolytic processing of plant aspartic proteases starts with removal of the signal sequence upon translocation to the ER lumen. The following conversion steps include cleavage of the prosegment and total or partial removal of the internal PSI domain to produce mature two-chain forms of the enzymes. In the mature two-chain form both polypeptide chains are held together by hydrophobic interactions and hydrogen bonds (see Simões and Faro (2004)[3]).

Plant Specific Insert (PSI)

Many plant aspartic proteases differ from their mammalian and microbial counterparts by the presence of a plant-specific insert (PSI) which is cleaved out during protein maturation to give rise to the mature, two-chain enzyme. The PSI typically has about 104 amino acids. In phytepsin, from barley, removal of the PSI led to secretion of the mutated phytepsin when expressed in Tobacco protoplasts, whilst retaining enzymatic activity[4]. The presence of PSI was shown to be at least necessary for vacuolar sorting[4]. The PSI of Cardosin A has been shown to be an inducer of vesicle leakage[18].

Vacuolar Sorting

The final destination of a protein after synthesis is a highly complex and regulated process and is usually dependent on the presence of specific targeting information (e.g. sorting signals, post-translational modifications) which is specifically recognized by receptors that target nascent proteins to their final localizations in the cell[1].

One of the most complex biosynthetic routes is the secretory pathway. In a very simplified way, this system comprises several membrane-bound subcellular compartments and proteins are exchanged between these compartments by vesicle trafficking. Proteins resident in the endoplasmic reticulum (ER), Golgi apparatus, vacuoles or plasma membrane/extracellular matrix have to enter this endomembrane system and some of them undergo processing and post-translational modifications along their passage through the ER and Golgi network. Targeting to ER is determined cotranslationally by the presence of a signal peptide at the N-terminus of a nascent protein[1]. Although recent evidence indicates that the system may be more complex than first expected[2], it is still generally accepted that proteins are actively sorted to vacuoles, meaning that they contain specific vacuolar sorting signals (VSS's).

Different types of vacuolar sorting signals (VSS's) have been identified[1,3]. Even though no consensus sequence has been yet defined for these signals they are currently divided into three categories: sequence-specific VSS (ssVSS's) which comprise N-terminal propeptides (e.g. sporamin) or internal sequences (e.g. ricin); C-terminal propeptides (CT-PP's) (e.g. lectin and chitinase) and physical structure VSS (psVSS's) [e.g. plant specific Insert (PSI) of phytepsin][3]. Given the number of soluble vacuolar proteins that lack these types of VSS's, it is expected that novel motifs for vacuolar sorting are yet to be identified.

The ability to manipulate protein sorting is particularly important if considering high value-protein expression in heterologous or homologous systems. Specifically sorting a selected protein to storage vacuoles may be highly advantageous for accumulation of large quantities of recombinant proteins and, thereby, increase the food value of a plant. Conversely, redirecting a native vacuolar protein for secretion may be particularly useful considering, for example, expression in heterologous systems like yeasts where protein secretion into the media greatly facilitates recombinant protein handling and purification.

The relevance of these vacuolar sorting signals in various applications is confirmed by different issued patents: US69723504, US73686285, US53607266 and US60546377, where the last two describe the VSS's of lectin and chitinase, respectively.

Typical aspartic proteases are widely distributed in plants and have been purified from a variety of tissues. In general, these enzymes share high levels of amino acid sequence identity (over 60%) and the majority of them accumulate inside plant vacuoles. However, there are exceptions to this intracellular localization and several plant aspartic proteases were shown to be extracellular[8].

Plant aspartic proteases have been used in cheese manufacture for many years. Indeed, this is amongst the earliest application of enzymes in food processing, dating back to approximately 6000 BC (see Fox and McSweeney 1999 cited in Claverie-Martin and Vega-Hernandez (2007)[19]). Plant extracts, including dried flowers, have been added to milk to act as a coagulant. Although efforts have been made to produce recombinant plant aspartic proteases, these are not yet commercially available due to the large volumes of culture or high number of culture steps to obtain a significant amount of recombinant protein.

SUMMARY OF THE INVENTION

The inventors have determined that the normal VSS function of the ~100 amino acid plant specific insert (PSI) may be inactivated by recombinant DNA manipulation to enhance secretion of plant aspartic proteases in either homologous or heterologous expression systems (preferably heterologous, non-plant, expression systems), whilst retaining the aspartic protease activity of the secreted protein. Thus, the inventors have provided a novel and advantageous means of producing high volumes of plant aspartic proteases in a form that is convenient to isolate and purify.

Accordingly, the present invention provides methods for the expression in cells of mutant plant aspartic proteases modified such that the PSI domain is inactivated, the expression preferably being in non-plant eukaryotic cells. Preferably, the mutant plant aspartic proteases retain their protease activity.

The present invention therefore provides a plant aspartic protease that is modified so as to lack a functional plant specific Insert (PSI) domain. The PSI domain may be entirely deleted, or partially deleted. For example, at least 60, at least 65, at least 70, at least 75, at least 80, at least 85, at least 90, at least 95, at least 100 or more amino acids of the PSI domain may be deleted. The number of amino acids deleted may be calculated by comparing the plant aspartic protease sequence or PSI domain sequence to the sequence of an unmodified plant aspartic protease, such as a wild-type plant aspartic protease. The PSI domain may be wholly or partially replaced with a linker, such as a linker of 1, 2, 3, 4, 5, 6, 7, 8, 9, 10 or more amino acid residues. The amino acids of the linker may be all the same, for example, they may all be glycine residues. Alternatively, the linker may comprise a plurality of different amino acids. However, this linker does not comprise all, or substantially all, the amino acid residues of the functional PSI domain. The modification to the PSI domain may confer altered trafficking on the plant aspartic protease. For example, trafficking of the plant aspartic protease within a cell may be modified as compared to the trafficking of a plant aspartic protease which does not have a modified PSI domain, such as a wild type plant aspartic protease. The plant aspartic proteases according to the invention have caseinolytic activity.

The plant aspartic protease according to the invention may have a pro segment. The N-terminal of the plant aspartic protease may not be modified with respect to, or different to, wild-type plant aspartic protease.

The plant aspartic protease according to the invention may be modified at the C-terminus. For example, the plant aspartic protease according to the invention may not have sequence AEAA or AEAV at the C-terminus.

The plant aspartic protease of the invention may be a modified cardosin, cyprosin, cenprosin, phytepsin, or cynarase. It may have a sequence of at least 70%, at least 75%, at least 80%, at least 85%, at least 90%, at least 95% or at least 98% sequence identity to a known cardosin, cyprosin, cenprosin, phytepsin, or cynarase sequence. In some cases, the plant aspartic protease may be a cardosin, such as cardosin A or cardosin B. In some cases, the plant aspartic protease according to the invention is cardosin B.

In some cases, the plant aspartic protease according to the invention has at least 70% identity to SEQ ID NO: 1 or SEQ ID NO: 2. In some cases, it has at least 75%, at least 80%, at least 85%, at least 90%, at least 95% or at least 98% identity to SEQ ID NO: 1 or SEQ ID NO: 2.

A plant aspartic protease according to the invention may have been expressed in a eukaryotic cell. For example, the plant aspartic protease may have been expressed in a yeast cell, for example a *Kluyveromyces lactis* cell. In some cases, the plant aspartic protease according to the invention has not been produced in a plant protoplast. In some cases the plant aspartic protease has not been produced in *E. coli*.

The invention also provides nucleic acid encoding a plant aspartic protease according to the invention. For example, nucleic acid encoding a plant aspartic protease which lacks a functional PSI domain; a polypeptide having amino acid sequence SEQ ID NO: 1, or SEQ ID NO: 2, or a polypeptide having at least 70% sequence identity to SEQ ID NO: 1, or SEQ ID NO: 2, wherein the polypeptide lacks a functional plant specific insert (PSI) domain. A vector comprising the nucleic acid is also provided, for example a yeast expression vector.

Also provided is a cell which encodes a plant aspartic protease according to the Invention. The cell may have a genome modified to encode the plant aspartic protease, or may include a vector that encodes the plant aspartic protease. The cell may have nucleic acid, for example, its genome may be modified to include nucleic acid, which encodes a plant aspartic protease which lacks a functional PSI domain; the polypeptide of SEQ ID NO: 1, or SEQ ID NO: 2, or a polypeptide having at least 70% sequence identity to SEQ ID NO: 1, or SEQ ID NO: 2, wherein the polypeptide encoded lacks a functional plant specific insert (PSI) domain. The cell may be a yeast cell, such as *Kluyveromyces lactis*.

The invention also provides a method for producing a plant aspartic protease in which a cell, preferably a cell which is not a plant cell, or a plant protoplast, or an *E. coli*, which expresses a plant aspartic protease which lacks a functional plant specific insert (PSI) domain.

In some methods the plant aspartic protease is secreted from the cell, and the method may comprise collecting the plant aspartic protease that has been secreted from the cell, for example by partitioning the secreted plant aspartic protease from other components secreted from the cell or otherwise contained within the media in which the cells are growing. The method may comprise expressing the plant aspartic protease from a vector contained within the cell, or from the genome of the cell. The cell may be a eukaryotic cell. The cell may be a fungal cell such as a yeast cell, for example *Kluyveromyces lactis*.

The plant aspartic proteases according to the invention may be used in clotting or coagulating milk, for example for use in making cheese. Thus, the invention further provides methods for clotting or coagulating milk, and/or for making cheese. The method may involve the use of more than one type of plant aspartic protease, such as a cardosin A and a cardosin B, one or more of which has been modified to lack a PSI domain.

The invention further provides a method for promoting the accumulation of a polypeptide of interest in the vacuole of a cell. The method may comprise expressing a polypeptide construct in the cell, the polypeptide construct comprising an amino acid sequence encoding the protein of interest covalently linked to an amino acid sequence encoding a PSI domain. For example, the PSI domain of cardosin A. The PSI domain may have at least 70% sequence identity to SEQ ID NO: 3 or SEQ ID NO: 4. Vectors comprising such constructs are also provided, along with cells that include such vectors, or cells which have been modified by such vectors to express the protein construct from their genome.

DESCRIPTION OF PREFERRED EMBODIMENTS

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 2. Sequences of Cardosins B and A with and without PSI sequence, PSI sequences, and sequences used in the examples.

FIG. 6. SDS-PAGE analysis of K-casein hydrolysis by cardosin A mutants. The enzymatic activity towards K-casein was tested at 37° C. for 2 hours.

DETAILED DESCRIPTION OF THE INVENTION

Figure 1:
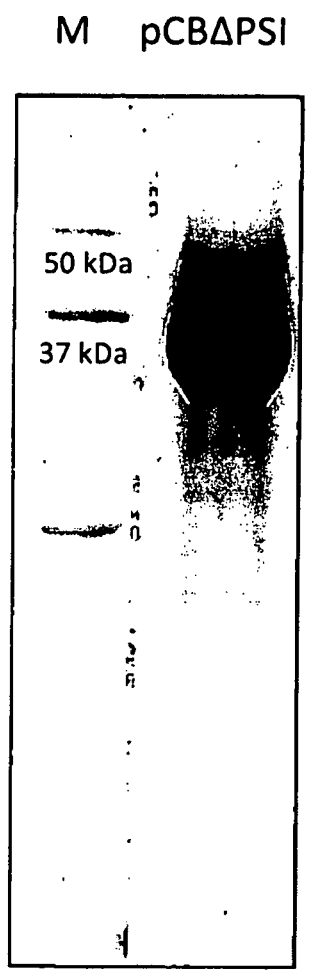
FIG. 1. SDS-PAGE gel electrophoresis of enzyme purified from *K. lactis* (pCBΔPSI).

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

Milk Clotting and Cheese Making

The use of aspartic proteases (Aps) in cheese manufacture is amongst the earliest applications of enzymes in food processing[17].

Enzymatic milk coagulation is a two-phase process. Stage one involves hydrolysation of $Phe^{105}$-$Met^{106}$ bond of bovine k-casein, splitting the protein molecule into two parts—para-k-casein (hydrophobic) and the macropeptide (hydrophilic). In the second phase, the para-k-casein micelles (which were destabilised during proteolysis) are coagulated.

As used herein, the term "clotting" is used interchangeably with "coagulating".

Chymosin, extracted from the abomasum of suckling calves, is specific for k-casein. However, Aps present in plant extracts cleave α, β and κ-caseins. This causes excessive acidity, bitterness and texture defects in cheese, but these characteristics are responsible for the special flavour, smell and consistency of the cheese varieties produced using these enzymes.

Methods of making cheese may involve adding a coagulant enzyme such as a plant aspartic protease to induce coagulation, separating the milk into solid curds and liquid whey. A plurality of different enzymes may be used, for example Cardosin A and Cardosin B. The plurality of different enzymes may be obtained from different sources, for example a plant aspartic protease and an aspartic protease of animal origin. Alternatively, the enzymes may be obtained from the same source. The curds are separated from the whey. "cutting" may be used to enhance the separation of the curds from the whey, by increasing the surface area of the curds. Salt may be added. The curds are then pressed, often into a mold, to further promote the separation of the curds from the whey. The pressed curds are then optionally wrapped, and left to ripen to form the mature cheese.

The plant aspartic proteases of the present invention are suited to the coagulation of milk and/or to cheese making because they may be readily produced in vitro, yet retain their specificity to κ-casein and ability to clot milk.

Plant Aspartic Proteases

In this specification a "plant aspartic protease" refers to and includes aspartic proteases that can be obtained from plant cells, or tissue, including whole plants. Plant aspartic proteases include cardosins, cyprosins, cenprosins, phytepsins and cynarases. In some cases, the plant aspartic protease according to the invention is not a phytepsin. As used herein the term "plant aspartic protease" includes mutants of such proteases, particularly mutants in which the PSI domain has been made non-functional. It is preferred that the mutation does not inactivate the aspartic protease function of the protein. In preferred embodiments the mutation is such that the resulting polypeptide retains at least 50%, more preferably one of at least 60%, 65%, 70%, 75%, 80%, 85%, 86%, 87%, 88%, 89%, 90%, 91%, 92%, 93%, 94%, 95%, 96%, 97%, 98% or 99% sequence identity with the amino acid sequence of the wild type aspartic protease.

The term "modified plant aspartic protease" as used herein describes a plant aspartic protease which contains one or more modifications as compared with a wild type plant aspartic protease. For example, it may contain one or more amino acid deletions, substitutions or additions as compared to the sequence of the plant aspartic protease as produced in a plant.

Cardosins are examples of plant aspartic proteases, obtained from cardoon (Cynara cardunculus). The amino acid sequence of Cardosin A and Cardosin B is known (see SEQ ID NOs: 5 and 6).

The inventors have developed a heterologous method of production for plant aspartic proteases in a GRAS yeast (K. lactis) that could be effectively transferred to scale-up production. They have used the K. lactis Protein Expression System from New England Biolabs and several optimization procedures were undertaken in order to enhance protein expression and secretion levels. Cardosin A and Cardosin B (a vacuolar and an extracellular aspartic protease from cardoon (Cynara cardunculus), respectively) were used as working models.

Although some trafficking mechanisms in plants appear to be similar to those in yeasts there are several variations, particularly regarding the presence in plants of multiple vacuole types, that could result in the non-recognition of aspartic protease VSS's by yeast vacuolar sorting receptors. In fact, other plant VSS's of the CTPP type were previously shown not to be recognized in yeasts. Conversely, the results described herein indicate that some VSS's identified in plant aspartic proteases are recognized by yeast trafficking mechanisms and can be used to redirect protein sorting. These results show that the PSI domain is functional in plants and yeasts.

Plant Specific Insert (PSI)

When the inventors generated a construct of Cardosin B (which is normally localised extracellularly), lacking the PSI domain and expressed this in the K. lactis yeast, higher levels of expression and secretion were observed in the absence of the PSI, when compared to the full-length wild type construct. These results demonstrate that removal of the PSI domain from all plant aspartic proteases (either vacuolar or secreted) may have a positive impact on their secretion, in yeasts or in plants.

The PSI is an insertion of approximately 100 amino acids located between the N-terminal domain and a C-terminal domain of the precursor "preproenzymes" of the majority of plant aspartic proteases so far identified. The PSI is only identified in plant aspartic proteases, and is highly similar to saposins and saposin-like proteins, whose biological function has not been completely established. Structurally, the PSI comprises five amphipathic α-helices folded into a compact globular domain and linked with each other by three disulphide bridges (discussed in Simoes and Faro 2004[3]). The PSI sequence shows no homology with mammalian or microbial aspartic proteases but is highly similar to that of saposin-like proteins (SAPLIPs). A unique feature of the PSI is the swap of the N- and C-terminal portions of the saposin-like domain, where the C-terminal portion of one saposin is linked to the N-terminal portion of the other saposin. Hence the PSI is not a true saposin but a swaposin.

The plant aspartic proteases described herein may lack a functional PSI domain. The PSI domain may be entirely or partially deleted, or mutated such that it is rendered non functional. Mutation may involve modification of an oligonucleotide sequence encoding the aspartic protease. For example, the modification may be an addition, deletion, insertion or substitution in the coding sequence.

A PSI domain may have substantial identity to SEQ ID NO: 3, or SEQ ID NO: 4. A PSI domain may have at least 70% identity, at least 75% identity, at least 80% identity, at least 85% Identity, at least 90% identity, at least 95% identity, at least 98% identity, or 100% identity to SEQ ID NO: 3 or SEQ ID NO: 4.

The PSI domain may have a length of any one of 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150, amino acids. The PSI domain may have a length in the range 80, to 120 amino acids, or 90 to 110 amino acids, or 95 to 105 amino acids, or 98 to 108 amino acids. The PSI domain may have a minimum length of about 80 amino acids, more preferably one of 81, 82, 83, 84, 85, 86, 87, 88, 89, 90, 91, 92, 93, 94, 95, 96, 97, 98, 99, 100, 101, 102, 103; 104, 105, or 106 amino acids. The PSI domain may have a maximum length of about 130 amino acids, more preferably one of 100, 101, 102, 103, 104, 105, 106, 107, 108, 109, 110, 111, 112, 113, 114, 115, 116, 117, 118, 119, 120, 121, 122, 123, 124, 125, 126, 127, 128, or 129 amino acids.

The PSI domain of a plant aspartic protease functions to regulate trafficking of cardosins in the cell, for example targeting the protein to the vacuole. Thus, plant aspartic proteases according to the invention, which lack a functional PSI domain have altered trafficking, for example as compared to plant aspartic proteases that contain a complete PSI domain. For example, a modified aspartic protease that lacks a functional PSI domain may not be targeted to the vacuole, whereas the unmodified aspartic protease, such as the wild type protein, might be targeted to the vacuole.

The skilled person may readily determine whether an aspartic protease lacks a functional PSI domain by any suitable method known in the art. For example agents known to affect protein trafficking (e.g. glycosidases) may be applied to a cell to determine whether trafficking of the modified aspartic protease is affected by the agent in the same or a similar way to the complete, or wild type, plant aspartic protease. Alternatively, or additionally, subcellular fractionation may be used to determine whether the modified and complete, or wild-type, aspartic proteases are present in a similar distribution within a cell. Alternatively, or additionally, immunocytochemistry may be used to determine whether the protein is secreted from the cell, or present in a different cellular compartment, to a complete, or wild type, plant aspartic protease.

The lack of a functional PSI domain may be sufficient to stop the plant aspartic protease collecting in the vacuole and/or to increase secretion of the plant aspartic protease from the cell. In some cases, the lack of a functional PSI domain may entirely prevent the plant aspartic protease being localised to the vacuole such that substantially all of the plant aspartic protease produced by the cell is secreted from the cell.

The plant aspartic acid which lacks a functional PSI domain may be any plant aspartic acid. Preferably, the plant aspartic acid is from the Cardosin family of plant aspartic proteases, i.e. a mutant or modified Cardosin that lacks a functional PSI domain. In some cases the plant aspartic protease may be further mutated.

Modification of the PSI domain to render it non-functional may affect the kinetic properties of the plant aspartic protease. For example, the modified plant aspartic protease may be less caseinolytic as compared to the naturally occurring, or wild-type, plant aspartic protease. In some cases, modification of the PSI may increase the specificity of the plant aspartic protease for a substrate. For example, it may increase the specificity of the plant aspartic protease for α-casein.

Pro Segment

The prosegment is located in the N-terminal of plant aspartic proteases. It is present in the precursor protein and is normally removed by proteolysis during production of the mature, active, enzyme from the Inactive zymogen. In some cases, the plant aspartic proteases according to the invention are expressed with a prosegment. The prosegment comprises approximately 44 amino acids.

C-Terminal Sequence

The C-terminal sequence Is a putative enzyme sorting signal. Certain plant aspartic proteases may lack 1, 2, 3, 4, 5, 6, 7, 8, 9 or 10 amino acid residues, preferably 4 amino acids, from the C terminus, as compared to the naturally occurring form of the aspartic protease. For example, modified cardosin A according to the invention may lack AEAA from the C-terminus and cardosin B may lack AEAV.

Linkers

As used herein, the term "linker" denotes a series of amino acid resides which are introduced into a protein sequence to replace amino acid residues which have been removed. For example, the plant aspartic proteases of the present invention lack a functional PSI domain. Where the PSI domain is fully or partially deleted from the plant aspartic protease of the invention, the deleted amino acids may be replaced by a linker. The linker may allow two or more regions of the protein containing it to fold into the correct three dimensional configuration.

The linker may comprise one or more amino acids. The amino acids may all be the same, for example a plurality of glycine residues. Alternatively, the amino acids may be different. The linker may comprise a sequence corresponding to a scrambled sequence of the PSI domain.

The linker may comprise between 1 and 100, between 1 and 50, between 1 and 25 or between 1 and 10 amino acids. The linker may comprise 2, 3, 4, 5, 6, 7, 8, 9 or 10 amino acids. In some cases, the linker consists of 1 to 7 amino acid residues.

The presence of a linker may affect the kinetic properties of the plant aspartic protease. For example, the Introduction of a linker may render the plant aspartic protease less caseinolytic as compared to the naturally occurring, or wild-type, plant aspartic protease. In some cases, the linker may increase the specificity of the plant aspartic protease for a substrate. For example, the introduction of a linker may increase the specificity of the plant aspartic protease for α-casein.

Cardosins

In this specification, a Cardosin nucleic acid may be any nucleic acid (DNA or RNA) having a nucleotide sequence which encodes a polypeptide having a specified degree of sequence identity to one of SEQ ID No.s 5 and 6 to an RNA transcript of any one of these sequences, to a fragment of any one of the preceding sequences or to the complementary sequence of any one of these sequences or fragments. Alternatively a Cardosin nucleic acid may be one that hybridises to one of these sequences under high or very high stringency conditions. The specified degree of sequence identity may be from at least 60% to 100% sequence identity. More preferably, the specified degree of sequence identity may be one of at least 65%, 70%, 75%, 80%, 85%, 86%, 87%, 88%, 89%, 90%, 91%, 92%, 93%, 94%, 95%, 96%, 97%, 98% or 99% identity.

In this specification, a Cardosin polypeptide may be any peptide, polypeptide or protein having an amino acid sequence having a specified degree of sequence identity to one of SEQ ID NO.s 1, 2, 5 or 6 or to a fragment of one of these sequences. The cardosin may be, or have a specified degree of sequence identity to, cardosin A as deposited at GenBank under accession number Q9XFX3.1 (GI: 75267434). The cardosin may be, or have a specified degree of sequence identity to, cardosin B as deposited at GenBank under accession number Q9XFX4.1 (GI: 75338567).

The specified degree of sequence identity may be from at least 60% to 100% sequence identity. More preferably, the specified degree of sequence identity may be one of at least 65%, 70%, 75%, 80%, 85%; 86%, 87%, 88%, 89%, 90%, 91%, 92%, 93%, 94%, 95%, 96%, 97%, 98% or 99% identity.

Sequence Identity

Percentage (%) sequence identity is defined as the percentage of amino acid residues in a candidate sequence that are identical with residues in the given listed sequence after aligning the sequences and Introducing gaps if necessary, to achieve the maximum sequence identity, and not considering any conservative substitutions as part of the sequence identity. Sequence identity is preferably calculated over the entire length of the respective sequences.

Alignment for purposes of determining percent amino acid sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

In certain aspects the invention concerns compounds which are isolated peptides/polypeptides comprising an amino acid sequence having a sequence identity of at least 60% with a given sequence. Alternatively, this identity may be any of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity.

Identity of nucleic acid sequences may be determined in a similar manner involving aligning the sequences and introducing gaps if necessary, to achieve the maximum sequence identity, and calculating sequence identity over the entire length of the respective sequences.

In certain aspects the invention concerns compounds which are isolated nucleic acids comprising a nucleotide sequence having a sequence identity of at least 60% with a given sequence. Alternatively, this identity may be any of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity.

Certain aspects of the invention relate to complete plant aspartic proteases (i.e. comprising substantially all domains present in the wild-type protein). For example, Cardosin A may have an amino acid sequence having a specified degree of sequence identity to SEQ ID NO: 3, or Cardosin B may have an amino acid sequence having a specified degree of sequence identity to SEQ ID NO: 4.

Preferably, the plant aspartic proteases of the invention lack a functional PSI domain. For example, Cardosin B may have an amino acid sequence having a specified degree of sequence identity to SEQ ID NO: 1, and Cardosin A may have an amino acid sequence having a specified degree of sequence identity to SEQ ID NO: 2.

A fragment may comprise a nucleotide or amino acid sequence encoding a portion of the corresponding full length sequence. In this specification the corresponding full length sequence may be one of SEQ ID No.s 1, 2, 5, or 6. Said portion may be of defined length, and may have a defined minimum and/or maximum length.

Accordingly, the fragment may comprise at least, i.e. have a minimum length of, 10, 11, 12, 13, 14, 15, 16, 17, 18, 19, 20, 25, 30, 40, 50, 60, 70, 80, 85, 90, 95, 96, 97, 98 or 99% of the corresponding full length sequence. The fragment may have a maximum length, i.e. be no longer than, 10, 11, 12, 13, 14, 15, 16, 17, 18, 19, 20, 25, 30, 40, 50, 60, 70, 80, 85, 90, 95, 96, 97, 98 or 99% of the corresponding full length sequence. The fragment may have a length anywhere between the said minimum and maximum length.

The fragment may comprise at least, i.e. have a minimum length of, at least 100, 120, 140, 160, 180, 200, 220, 240, 260, 280, 300, 320, 340, 360, 377, 380, 383, 400, 420, 440, 460, 480 or 500 amino acids. The fragment may have a maximum length, i.e. be no longer than, 220, 240, 260, 280, 300, 320, 340, 360, 377, 380, 383, 400, 420, 440, 460, 480 or 483 amino acids.

In some embodiments the plant aspartic protease may be a mutant or modified plant aspartic protease, such as a mutant or modified Cardosin. The plant aspartic protease may be mutated relative to the wild-type or genomic plant aspartic protease, carrying one or more alterations to the nucleic acid encoding the plant aspartic protease and/or to the amino acid sequence of the plant aspartic protease. The alteration may take the form of an addition, insertion, substitution or deletion.

In some embodiments of the Invention the plant aspartic protease is mutated such that it does not have a functional PSI domain. In some cases, the PSI domain is entirely or substantially absent. In others at least one mutation is included in the protein and/or nucleic acid sequence such that the PSI domain of the aspartic protease is not fully transcribed, is Incorrectly transcribed, or is otherwise non functional. Mutations may be point mutations or larger mutations, wherein one or more base pairs of the nucleic acid sequence encoding the aspartic protease are added, substituted, deleted or inserted. In some cases, the mutation is one that causes the subsequent nucleic acids to be transcribed out of frame, thereby producing a non-functional protein product. In other cases, mutation of a single base pair causes an alteration in the protein sequence such that the protein product is non functional. Where the mutation causes subsequent nucleic acids to be transcribed out of frame it may be necessary to include a further change downstream of the first mutation in order to restore transcription of a subsequent part of the protein, e.g. after some or all of the PSI domain, back into frame.

Methods for introducing mutations are known in the art, and the skilled person will readily appreciate suitable methods for creating a modified or mutant plant aspartic protease according to the invention. Preferably, mutations are Introduced by site directed mutagenesis, for example through PCR mutagenesis. PCR mutagenesis is a method for generating point mutations on a double stranded plasmid and involves the use of two synthetic oligonucleotide primers containing the desired mutation, each complementary to the opposite strands of a vector containing the plant aspartic protease to be mutated.

Methods of Producing a Plant Aspartic Protease

Plant aspartic proteases may be produced according to any method known in the art, such as microbial fermentation, plant, insect or mammalian cell culture.

Certain methods according to the invention involve expressing a plant aspartic protease that lacks a functional PSI domain in a cell. The method optionally further comprises the step of collecting plant aspartic protease that has been secreted from the cell.

Molecular biology techniques suitable for the producing plant aspartic proteases according to the invention in cells are well known in the art, such as those set out in Sambrook et al., *Molecular Cloning: A Laboratory Manual*, New York: Cold Spring Harbor Press, 1989

The plant aspartic protease may be expressed from a nucleotide sequence encoding the plant aspartic protease. The nucleotide sequence may be contained in a vector present in the cell, or may be incorporated into the genome of the cell.

A "vector" as used herein is an oligonucleotide molecule (DNA or RNA) used as a vehicle to transfer foreign genetic material into a cell. The vector may be an expression vector for expression of the foreign genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express plant aspartic proteases from a vector according to the invention. Suitable vectors include plasmids, binary vectors, viral vectors and artificial chromosomes (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing plant aspartic proteases according to the invention. The cell may be a prokaryote or eukaryote. Preferably the cell is a eukaryotic cell such as a yeast cell, a plant cell, insect cell or a mammalian cell. In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

In some embodiments the cell is not a plant cell, or a plant protoplast cell.

In some preferred embodiments the cell is a fungi (including yeasts and molds) or microbial eukaryote, or single cell eukaryote, preferably a yeast of the genus *Kluyveromyces, Rhizomucor, Endothia, Apergillus* or *Saccharomyces*.

Suitable yeast cells include *Kluyveromyces lactis, Kluyveromyces marxianus, Rhizomucor meihei, Endothia parasitica, Rizomucor pusillus, Pichia pastoris, Aspergillus*

*niger, Apsergillus oryzae* and *Saccharomyces cerevisae*. The yeast may be a GRAS (Generally Regarded As Safe) yeast, i.e. a yeast that has GRAS status from the Food and Drug Administration (FDA).

Methods of producing the plant aspartic protease may involve culture or fermentation of a eukaryotic cell modified to express the plant aspartic protease. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted aspartic protease. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express a plant aspartic protease, the plant aspartic protease is preferably isolated. Any suitable method for separating proteins from cell culture known in the art may be used. In order to isolate a protein of interest from a culture, it may be necessary to first separate the cultured cells from media containing the protein of interest. If the protein of interest is secreted from the cells, the cells may be separated from the culture media that contains the secreted protein by centrifugation. If the protein of interest collects within the cell, for example in the vacuole of the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the protein of interest.

It may then be desirable to isolate the protein of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation, or may be performed subsequently to precipitation.

Once the protein of interest has been isolated from culture it may be necessary to concentrate the protein. A number of methods for concentrating a protein of interest are known in the art, such as ultrafiltration or lyophilisation.

A plant aspartic protease that has been isolated from a cell may be mixed with a carrier, adjuvant or diluent to form a product comprising a composition containing the plant aspartic protease. The product formed may be of any kind, e.g. liquid, solid, powder, cream and may be suitable for at least any of the following uses: as a detergent or washing powder, as a food modifier, as a meat tenderiser, as a milk coagulant, as a stain remover, as a leather softener, as a rennet substitute.

Methods for Promoting Accumulation of a Polypeptide of Interest

The invention also provides methods for promoting the accumulation of a polypeptide of interest in the vacuole of a cell, particularly a plant cell. Such methods involve expressing a polypeptide construct in the cell, the construct comprising the amino acid sequence of the polypeptide of interest and the amino acid sequence of a PSI domain. The amino acid sequences are preferably covalently linked to form a single contiguous amino acid sequence forming the polypeptide construct. As such, in some embodiments, the polypeptide construct may be a fusion protein.

The PSI domain may be included in the amino acid sequence of the construct at any position. In some embodiments the PSI domain may be added at any one of the N-terminus, C-terminus or a position between the N- and C-termini.

The polypeptide of interest can be any polypeptide, but is preferably not a polypeptide that normally (i.e. in the wild type sequence) encodes a PSI domain. For example, in some embodiments the polypeptide of Interest is not an aspartic protease, and in some embodiments the polypeptide of interest is not a plant aspartic protease.

The polypeptide of interest Is preferably a polypeptide that forms a protein having a measurable activity, e.g. binding to another molecule, or enzyme activity. The polypeptide construct preferably retains such a measurable activity, although the level of activity may be reduced or increased compared to the wild type polypeptide of interest. As such, the polypeptide will typically have a minimum length of at least about 50 amino acids, and more preferably one of about 60, 70, 80, 90, 100, 110, 120, 130, 140, 150, 160, 170, 180, 190, 200, 210, 220, 230, 240, 250, 260, 270, 280, 290, or 300 amino acids.

In some other embodiments the polypeptide of interest may be a small peptide, and may have a length of less than about 50 amino acids.

The polypeptide construct may be expressed from a nucleotide sequence encoding the polypeptide construct. The nucleotide sequence may be contained in a vector present in the cell, or may be incorporated into the genome of the cell.

Molecular biology techniques suitable for the producing plant aspartic proteases according to the invention in cells are well known in the art, such as those set out in Sambrook et al., *Molecular Cloning: A Laboratory Manual*, New York: Cold Spring Harbor Press, 1989

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

EXAMPLES

Example 1—Synthesis of Cardosin B in *K. lactis*

Strains and Growth Conditions

All plasmid constructions and propagations were performed using the *Escherichia coli* strain Top10F' (Invitrogen). The bacterial cells were grown at 37° C. in LB (Miller's Formulation—Invitrogen) liquid and solid (1.5% agar) medium, supplemented with ampicillin at 100 µg/ml (GE-Healthcare). The *Kluyveromyces lactis* GG799 strain was purchased from New England Biolabs and used as host strain to the recombinant protein expression studies. *K. lactis* cells were grown and maintained in YPD media (2% bactopeptone, 1% yeast extract, 2% glucose) whereas the expression experiments were performed in YPGal (2% bactopeptone, 1% yeast extract, 4% galactose) as culture media, both at 30° C. with shaking. The recombinant *K. lactis* cells were selected on solid Yeast Carbon Base (New England Biolabs) supplemented with 5 mM acetamide (New England Biolabs) plates.

proCardosinBΔPSI pKLAC1 Sub Cloning

The cloning and subcloning procedures were performed according to the manufacturers' instructions and using standard molecular biology cloning techniques. The construct proCardosinB lacking the PSI region (pCBΔPSI, also referred to herein as Bwo) was amplified by PCR, using the construct pCBΔPSI/TA as template, In order to introduce upstream and downstream of the cDNA the restriction sites XhoI and SalI, respectively. The pair of oligonucleotides used in the PCR reaction were:

```
pCB-XhoI
(CTCGAGAAAAGAATGGTCTCCAACGGCGGATTGCTTC
[SEQ ID NO: 7])
and pCB-SalI
(GTCGACTCAAACTGCTTCTGCAAATCCCACTCGTAAC
[SEQ ID NO: 8]).
```

After amplification the PCR product was cloned into pGEM (Promega) cloning vector and afterwards subcloned into the integrative expression pKLAC1 (NEB). The subcloning process was performed by cleavage/ligation at the XhoI/SalI restriction sites, resulting in pCBΔPSI cloning in frame with the α-mating factor secretion leader sequence.

*K. lactis* Recombinant Strains Construction

The recombinant plasmid pCBΔPSI/pKLAC1 was linearized by SacII (NEB) digestion, in order to obtain the insertion cassette fragments that were afterwards used in *K. lactis* transformation step. A total of 2 µg DNA was used in *K. lactis* GG799 transformation. This process was performed by electroporation with a "Gene Pulser" (BioRad) apparatus, using the following electroporation conditions: 1.5 KV, 25 mF and 200 Ohm. The positive transformants were selected based on their ability to growth on YCB acetamide media, and the multi-integrants clones selected by whole-cell PCR, following the instructions described on the "*K. lactis* expression Kit" protocols (NEB).

Heterologous pCBΔPSI Mutants Expression and Purification

An integrative recombinant *K. lactis* clone was selected for pCBΔPSI construct and was grown in YPD media, at 30° C. with shaking, for 16 h. The cultures were diluted to an OD600 nm of 0.3 in YPGal media and incubated at 30° C., with shaking for 4 days. Thereafter the cultures were centrifuged and the supernatants sequentially filtered through 0.8 µm, 0.45 µm and 0.2 µm filters. The samples were concentrated and activated by dilution 1:10 with 0.5M sodium acetate buffer pH4.0, at 37° C. A size exclusion chromatography was the first purification step. The samples were applied to a S200 26/60 column (GE-Healthcare) and the proteins were eluted with buffer 20 mM Tris-HCl pH7.5, 0.1M NaCl at a flow rate of 1 ml/min.

The fractions with milk clotting activity were pooled and applied to an ionic exchange on a Mono Q, using the buffer 20 mM Tris-HCl pH7.5. The proteins were then eluted with a linear gradient of 0-0.5M NaCl, at a flow rate of 0.75 ml/min. Both expression and purification procedures were followed by SDS-PAGE analysis (see FIG. 1).

Milk Clotting Activity Assays

The milk clotting activity was tested by using a skim milk solution at 12% in 10 mM $CaCl_2$. The supernatants and the purified fractions were mixed with the milk solution and incubated at 37° C. The clotting time was determined by visual observation.

This expression and purification method results in the production of a plant origin-based enzyme in considerable amounts (3 mg/L) and with a high purity level.

Example 2—Milk Clotting Activity of Recombinant Cardosin

VRen Preparation

The recombinant strain described in Example 1 was grown in YPD medium and the enzyme expression was induced by changing the medium to YPGal. After enzyme production, the culture medium was isolated from the cellular material by centrifugation and filtration, and it was acidified to pH 5.0 in order to activate the enzyme (this processed supernatant is the rennet preparation and it is hereby named VRen). The VRen used in the milk clotting studies using raw and pasteurized milk, was additionally subjected to a concentration step.

Study of the Milk Clotting Activity of VRen Using Skim Milk

The milk clotting activity of VRen was initially tested using a skim milk solution, in test tubes, at 37° C. A sample of 100 µl culture medium resultant from pCB construct expression in a yeast expression system, was added to 1 ml of 12% skim milk solution prepared in 10 mM $CaCl_2$. The mixture was incubated at 37° C. and the milk clotting time was determined by visual observation. The milk coagulation occurred after an Incubation time of approximately 30 minutes.

Study of Milk Clotting Activity of VRen Using Raw and Pasteurized Milk

Figure 3:
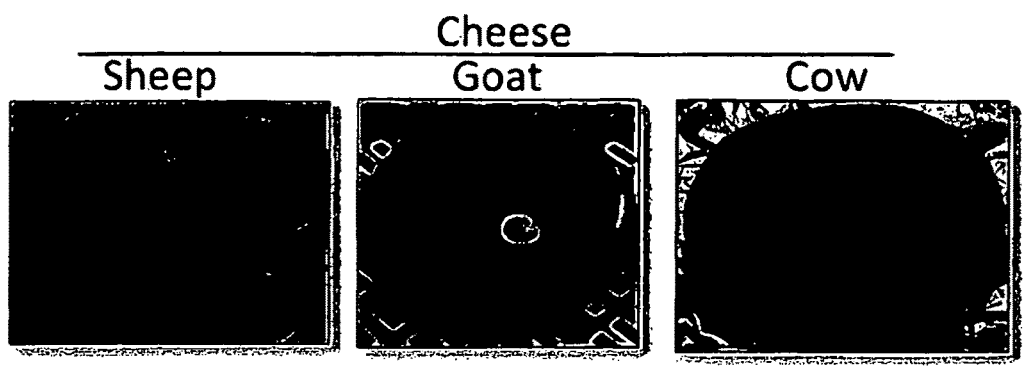
FIG. 3. Sheep, goat and cow cheeses produced using VRen as milk clotting agent.

The cheese manufacture using VRen as milk clotting agent was tested using three types of milk: sheep, goat and cow and the cheesemaking procedure was similar for all types of cheeses. Each cheese was produced by using 3 L of milk, and depending on the milk type different quantities of VRen were used (table I) in order to obtain a clotting time of approximately 40 minutes. The process was initiated by the addition of both VRen and salt (15 g/L) to the milk sample and subsequently incubation of the mixture in a water-bath at 32° C., allowing the curd formation and syneresis initiation. Once formed, the curd was cut both ways—horizontally and vertically—with a spatula, accelerating the syneresis process. The release of the whey from the curd was allowed to occur for another 5 minutes, preceding the whey draining and curd pressing process. After a manual pressing in plastic moulds, the curd was compressed using a press resulting in the complete release of the whey. Finally, the cheese was incubated in a maturation chamber for three weeks (FIG. 3).

TABLE I

Amount of VRen used in the coagulation process of different types of milk

| Milk | Enzyme (mg)/Milk (L) | Enzyme (mg)/Cheese (kg) |
|---|---|---|
| Goat (raw) | 3.1 | 31.4 |
| Sheep (raw) | 1.5 | 10.2 |
| Sheep (pasteurized) | 1.4 | 8.4 |
| Sheep (Bordaleira) | 2.0 | 10.3 |
| Cow (pasteurized) | 6.6 | 56.4 |

Example 3—Kinetic Properties of Modified Cardosin

Using the fluorogenic peptide (MCA)Lys-Lys-Pro-Ala-Glu-Phe-Phe-Ala-Leu-Lys(DNP) the kinetic properties of the truncated cardosin produced in Example 2 were compared with native cardosin B. The observed differences suggest that this truncated construct is less efficient in cleaving this substrate, in comparison with native cardosin B.

TABLE II

Kinetic parameters of modified versus wild type cardosin B

| | Km (uM) | VMax (umol/sec) | kcat (sec−1) | kcat/Km (uM−1 sec−1) |
|---|---|---|---|---|
| nCB | 1.4 | 6.36 × 10−6 | 24 | 17.1 |
| pCBΔPSI | 8.7 | 2.15 × 10−5 | 36.5 | 4.2 |

Thus, the introduction of a 3 Gly linker in place of the PSI domain changes the kinetic parameters of cardosin B and thus the catalytic efficiency of the enzyme.

Figure 4:
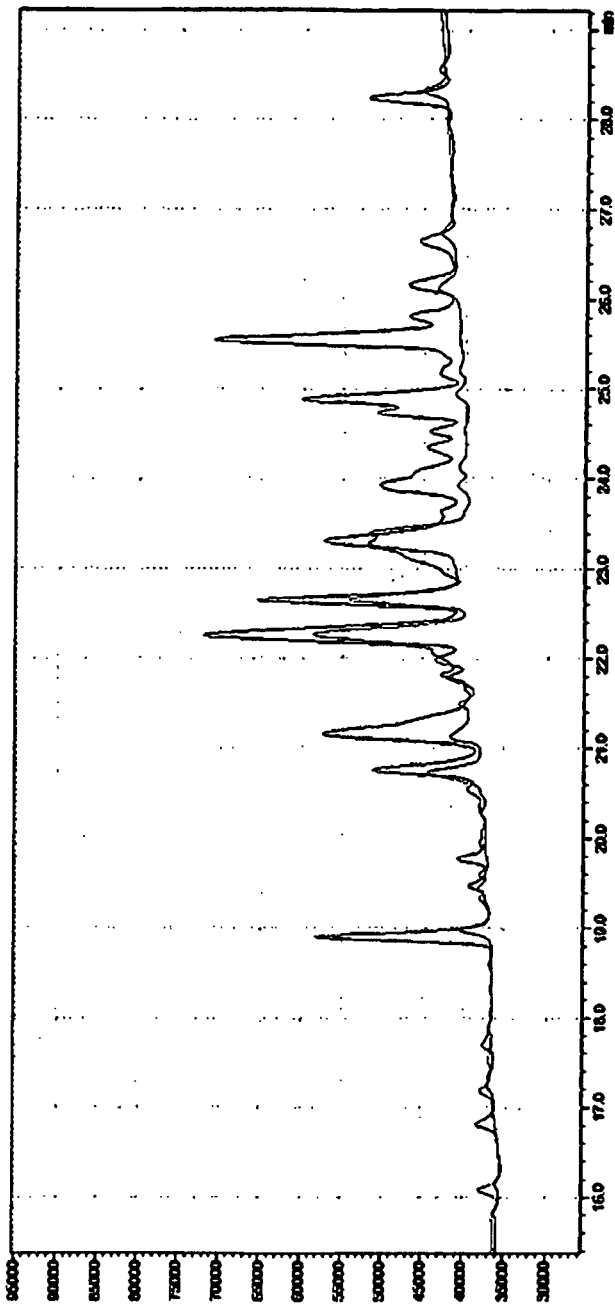
FIG. 4. RP-HPLC analysis of α-casein digestion products. Digestion by native cardosin B (nCB) is shown in black whereas digestion by recombinant cardosin B is shown in grey.

Differences in specificity between recombinant single-chain cardosin B produced in this work and native cardosin B were observed when specificity profiles towards α-casein were compared by RP-HPLC. See FIG. 4.

Recombinant cardosin B (pCBΔPSI) displayed a more restricted specificity towards this milk protein which results in the formation of a reduced number of proteolytic fragments in comparison with native cardosin B (nCB, black line).

Thus, the presence of the linker altered, but did not prevent, enzymatic activity.

Example 4—Modified Cardosin A Constructs

Figure 5A:
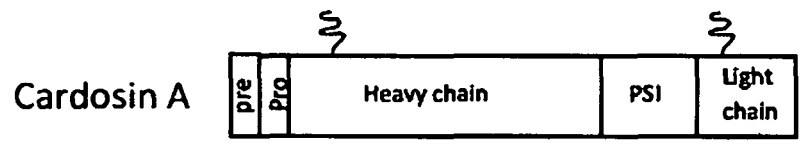
Figure 5B:
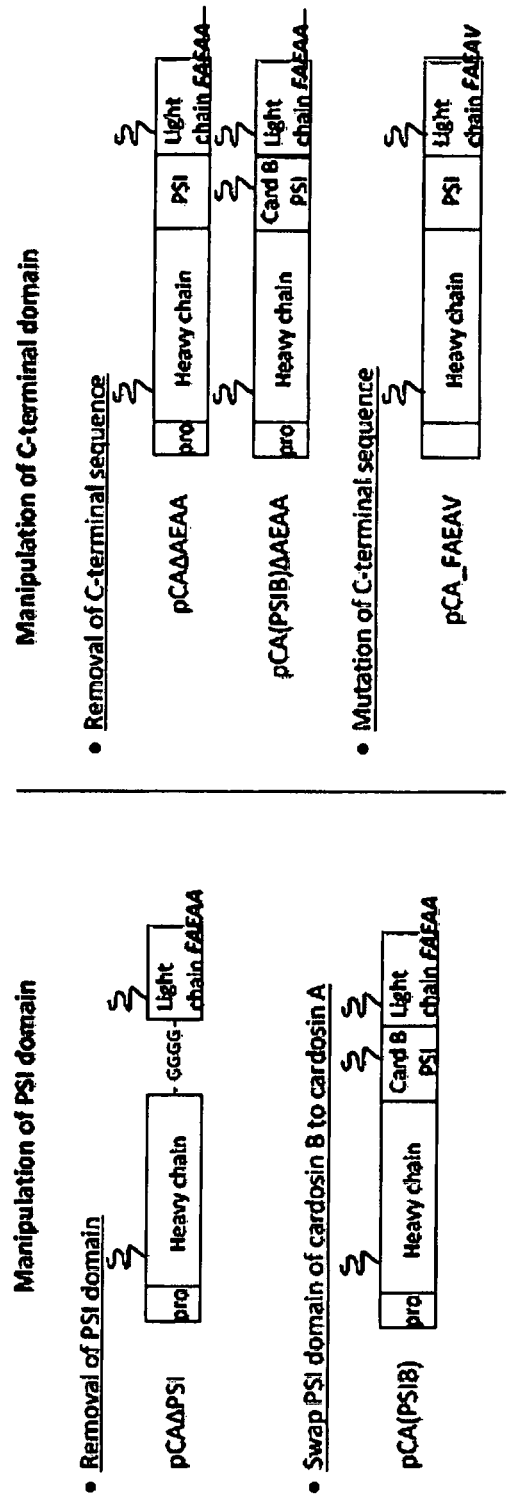

A strategy to enhance the secretion levels of recombinant cardosin A has been developed in order to improve the production yield. This strategy has comprised the manipulation of two regions of the enzyme: the PSI domain and the C-terminal region. Different mutants of cardosin A were constructed, by protein engineering, as shown in FIG. 5, and as set out in Table III.

TABLE III

Description of Cardosin A constructs

| Group | Construct | Description |
|---|---|---|
| Manipulation of PSI domain | pCAΔPSI | Deletion of PSI region |
| Manipulation of PSI domain | pCA(PSIB) | Swap of PSI domain of cardosin B to cardosin A |
| Manipulation of C-terminal domain | pCAΔAEAA | Deletion of C-terminal sequence (AEAA) |
| Manipulation of C-terminal domain | pCA(PSIB) ΔAEAA | Deletion of C-terminal sequence (AEAA) of pCA(PSIB) construct |
| Manipulation of C-terminal domain | pCA_FAEAV | Mutation of C-terminal amino acid to a valine, in order to mimic the C-terminal sequence of cardosin B |

Production of Recombinant Mutants of Cardosin A

The constructs were obtained by standard recombinant DNA methodologies and the cDNA of each construct was introduced into genomic DNA of *K. lactis*. The integration was performed by homologous recombination, confirmed by colony PCR and then several clones of each construct were randomly selected for protein production. After enzyme production in YPGal medium, the cultures were isolated from the cellular material by centrifugation and then acidified to pH 4.5, in order to activate the recombinant enzyme. These activated samples were used in κ-casein hydrolysis experiments. For milk-clotting studies the activated samples were additionally subjected to a concentration step.

Milk-Clotting Activity of Cardosin A Constructs

The milk-clotting activity of each construct was tested using a skim milk solution, in test tubes, at 37° C. An aliquot (100 μl) of activated and concentrated sample was added to 1 ml of 12% skim milk solution prepared in 10 mM $CaCl_2$. The mixture was incubated at 37° C. and the milk-clotting time was determined by visual observation.

TABLE IV

Milk-clotting activity of different cardosin A constructs

| Construct | Concentration | Milk clotting time |
|---|---|---|
| pCAΔPSI | 40x | 60 min |
| pCAΔAEAA | 20x | 50 min |
| pCA_FAEAV | 10x | 90 min |
| pCA(PSIB) | 20x | 30 min |

Some clones of the different constructs were able to clot skim milk, at an acceptable milk-clotting time (Table IV).

Hydrolysis of κ-Casein by Cardosin A Constructs

Proteolysis of κ-casein by recombinant enzymes was studied by SDS-PAGE. Commercial κ-casein was dissolved in water and then diluted in 0.1 M sodium phosphate buffer pH 6.8, to a final concentration of 0.3 mg/ml. Extract samples (0.25 μl per μl of reaction volume) were incubated with κ-casein and the digestion reaction was allowed to proceed at 37° C., for 2 hours. The reactions were stopped by heating the samples at 90° C., for 10 minutes, in the presence of denaturant solution. The digestions were analyzed by SDS-PAGE.

Figure 6:
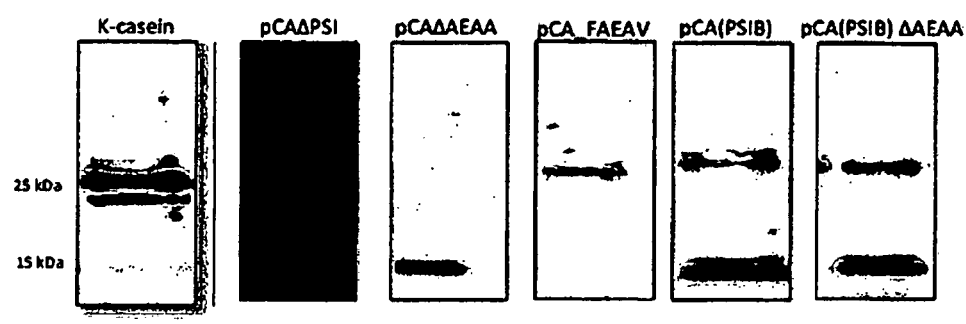
FIG. 6. Schematic representation of different constructs of cardosin A. A) Representation of primary structure of cardosin A. B) Schematic representation of cardosin A mutants.

The caseinolytic activity of cardosin A constructs was demonstrated by detection of a 15 kDa band after the incubation period. As shown in FIG. 6, the enzymatic activity towards κ-casein was slower for clone pCA_FAEAV.

Conclusions:

This study revealed that manipulation of PSI and/or C-terminal regions of cardosin A has improved enzyme production to detectable levels. The manipulation of these regions resulted in the production of cardosin A mutants with milk-clotting activity and enzymatic activity towards κ-casein.

Our data support the prediction that PSI acts as a vacuolar sorting signal because it was possible to detect milk-clotting activity/κ-casein digestion with the constructs where the PSI domain of cardosin A was absent or swapped with the sequence of the PSI domain of cardosin B, which is consistent with increased cardosin A secretion. Because cardosin B is an extracellular enzyme we hypothesised that cardosin B PSI domain could be differentially recognized/processed during protein transport and our results with pCA(PSIB) and pCA(PSIB)ΔAEAA further corroborate this initial assumption.

TABLE V

Summary of collected data.

| Construct | Positive clone/ total clones | Milk-Clotting (sample concentration, time) | Enzymatic activity (κ-casein) |
|---|---|---|---|
| pCAΔPSI | 1/20 | [40x], 60' | ✓ |
| pCAΔAEAA | 1/21 | [20x], 50' | ✓ |
| pCA_FAEAV | 5/10 | [10x], 90' | ✓ |
| pCA(PSIB) | 19/20 | [20x], 30' | ✓ |
| pCA(PSIB)ΔAEAA | 8/10 | — | ✓ |

Example 6—Modified Cardosin B Constructs

Figure 7:
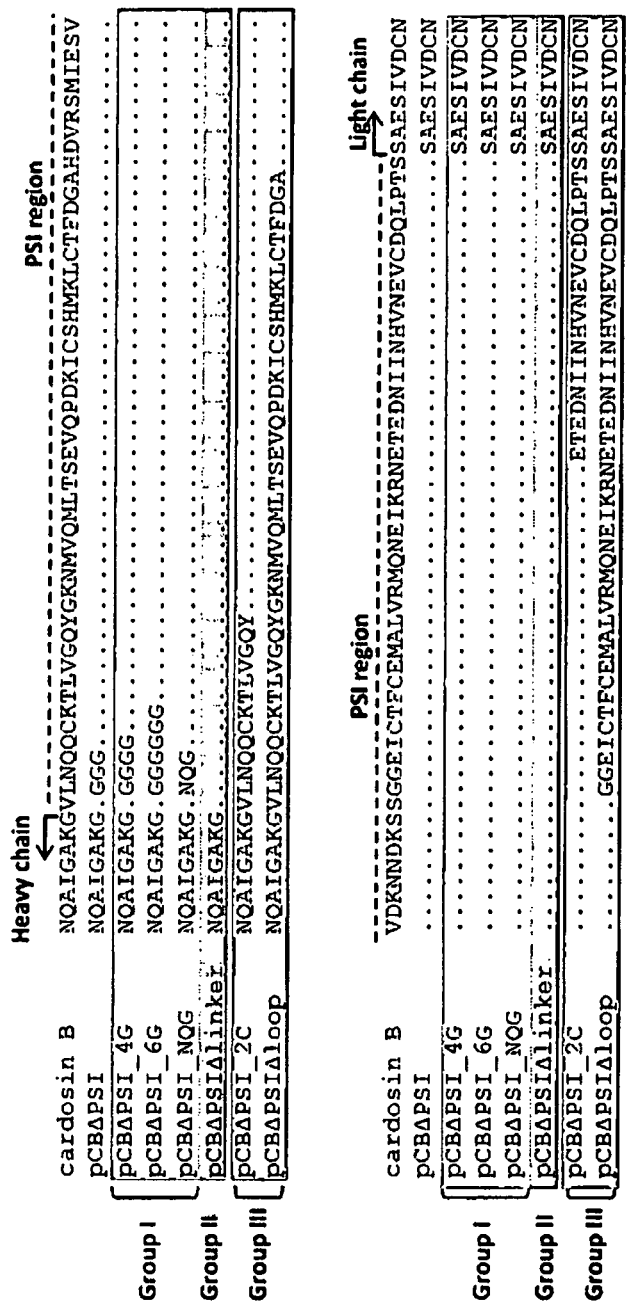
FIG. 7. Alignment of partial amino acid sequences of cardosin B constructs. The sequences correspond to the PSI/linker regions of each construct.

The following cardosin B constructs were tested:
Group I: deletion of the entire PSI domain+linkers of different sizes and sequences
Group II: deletion of the entire PSI domain with no linker
Group III: partial deletion of the PSI domain+/−different linkers
List of Constructs The pCBΔPSI clone (VRen) contains a linker of 3 Glycine residues between the heavy chain and light chain of enzyme. Based on this, different mutants were designed for each group of constructs as shown in Table VI below. An alignment of partial sequences of the construct corresponding to the PSI/linker region of each construct is shown in FIG. 7.

TABLE VI

Description of cardosin B constructs

| Group of constructs | Clone | Description |
|---|---|---|
| I | pCBΔPSI_4G | Linker with different size (4 Glycine residues) |
| I | pCBΔPSI_6G | Linker with different size (6 Glycine residues) |
| I | pCBΔPSI_NQG | Linker with same size but different sequence (NQG) |
| II | pCBΔPSIΔLK | Deletion of the entire PSI domain (without linker) |
| III | pCBΔPSI_2C | Partial removal of PSI: construct identical to the activated form of recombinant cardosin A, produced in E. coli expression system |
| III | pCBΔPSIΔloop | Partial removal of PSI: the PSI domain is composed by 5 α-helices and a loop region localized between the third and fourth α-helices. This construct contains a PSI without the loop region. |

Molecular Cloning of Cardosin B Constructs and Recombinant Enzyme Production.

All mutants, excepting both pCBΔPSI_2C and pCBΔPSIΔloop, were obtained by site-directed mutagenesis using the clone pCBΔPSI as template and a pair of primers adequate for each construction. The constructs pCBΔPSI_2C and pCBΔPSIΔloop were obtained using the cross-over PCR technique, with an appropriate pair of primers and cDNA of cardosin B as template. The cDNA of each construct was introduced into genomic DNA of expression yeast, by homologous recombination. The integration was confirmed by colony PCR and ten clones of each construct were randomly selected for protein production in YPGal medium. After enzyme production, the culture medium was isolated from the cellular material by centrifugation and then acidified to pH 4.5, in order to activate the enzyme. These activated samples were used in the following experiments.

Analysis of the Expression Levels by Western Blot

Figure 8:
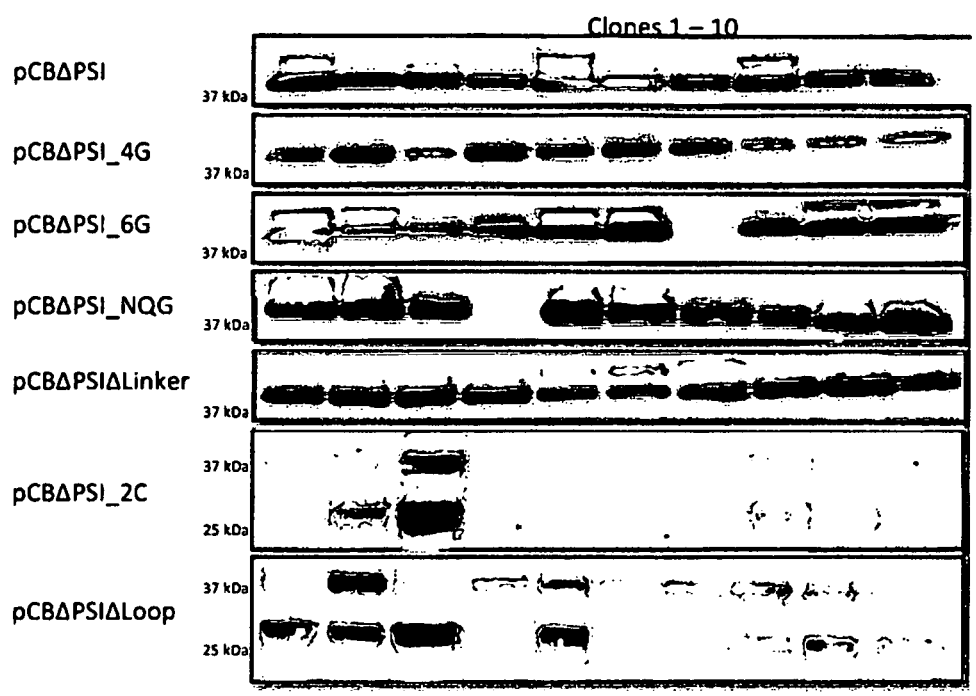
FIG. 8. Western-blot analysis of secreted cardosin B mutants. Activated samples (36 μl) from ten randomly selected clones of each construct were examined using a specific antibody against cardosin B).

The expression of cardosin B mutants was observed by Western blot. Samples were incubated with denaturant solution and loaded in 12.5% polyacrylamide gels for SDS-PAGE. Following electrophoretic separation, proteins were blotted into a PVDF membrane and immunodetected using an antibody specific for cardosin B (see FIG. 8). The results have shown that all constructs were expressed and secreted, however some differences in the secretion levels were observed. Both constructs pCBΔPSI_2C and pCBΔPSIΔloop (group III) displayed lower levels of secretion in comparison with the remaining constructs, suggesting an influence of the PSI region in the secretion levels of the enzyme. Moreover, the processing of these constructs is also different, with the detection of a band with lower molecular weight.

Hydrolysis of κ-Casein by Cardosin B Constructs

Proteolysis of κ-casein by recombinant enzymes was studied by SDS-PAGE. Commercial κ-casein was dissolved in water and then diluted in 0.1 M sodium phosphate buffer pH 6.8, to a final concentration of 0.3 mg/ml. Extract samples (0.05 μl per μl of reaction volume) were incubated with κ-casein and the digestion reaction was allowed to proceed at 37° C., for 15 minutes. The reactions were stopped by heating the samples at 90° C., for 10 minutes, in the presence of denaturant solution. The digestions were analyzed by SDS-PAGE.

Figure 9:
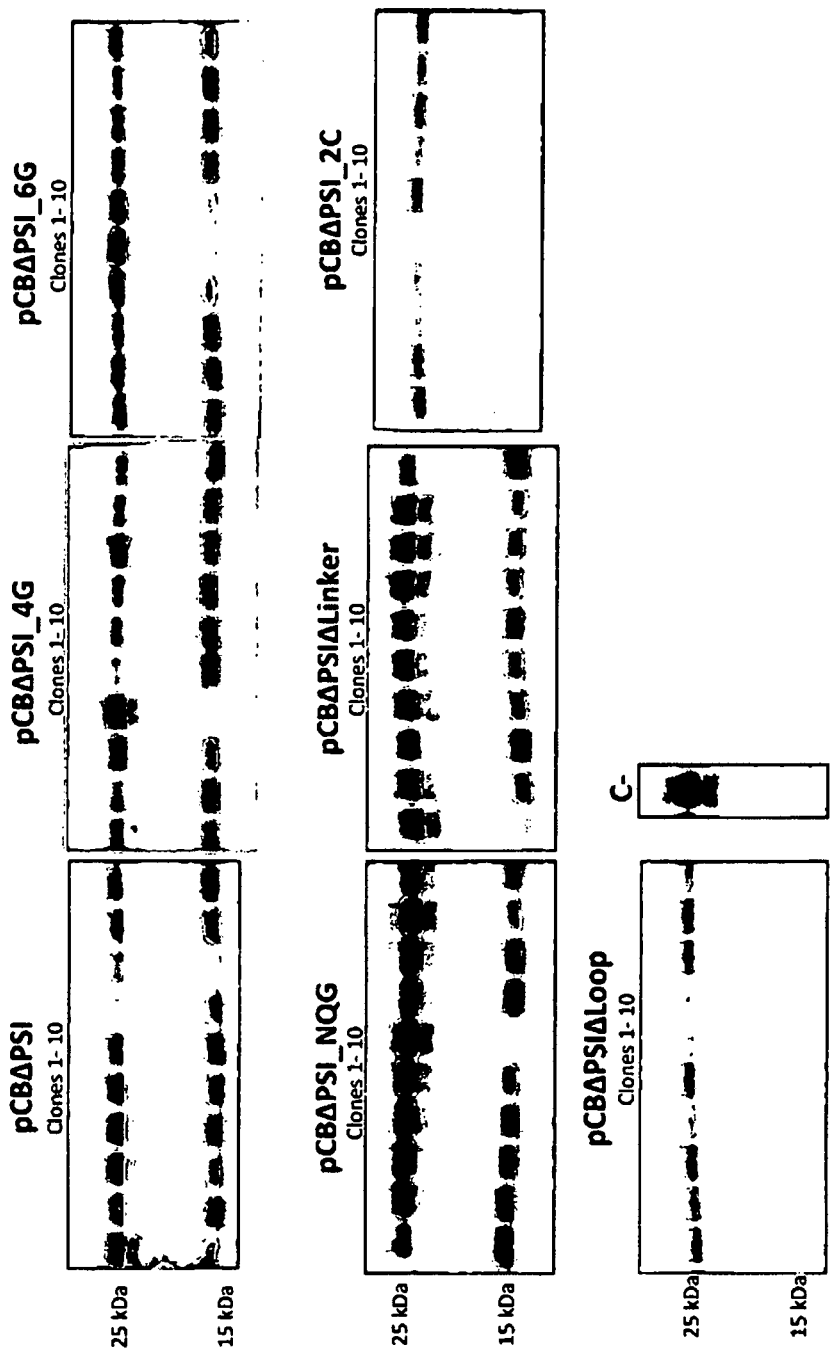
FIG. 9. SDS-PAGE pattern of K-casein hydrolysed by different constructs of cardosin B. K-casein (6 μg) was incubated at 37° C., for 20 minutes with a sample (1 μl) of each cardosin B mutant. A negative control performed in a parallel experiment, by incubating K-casein with culture supernatant (1 μl) of non transformed yeast cells (C–).

After the incubation period, a band of about 15 kDa was observed (para-κ-casein) for all reactions. The proteolysis was slower for pCBΔPSI_2C and pCBΔPSIΔloop probably due to the reduced secretion levels of these constructs (as shown in FIG. 9).

Milk-Clotting Activity of Cardosin B Constructs

Figure 10:
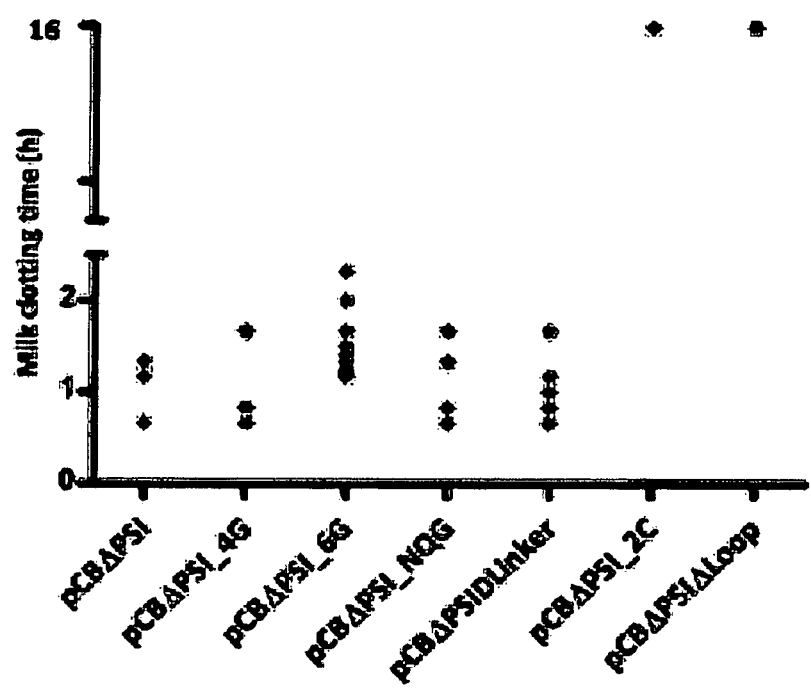
FIG. 10. Milk-clotting activity of cardosin B mutants. The milk-clotting activity was determined by mixing a skim milk solution (12%) prepared in 10 mM $CaCl_2$ with the active recombinant enzymes. The same ten randomly selected clones analysed in western bot and k-casein cleavage were tested for milk-clotting activity. The incubations were performed at 37° C. and the milk-clotting time determined by visual observation. Clones of the same construct with similar milk-clotting times are represented only by one dot.

The milk-clotting activity of each construct was tested using a skim milk solution, in test tubes, at 37° C. A sample of 100 μl culture medium resultant from pCB construct expression in a yeast expression system, was added to 1 ml of 12% skim milk solution, prepared in 10 mM $CaCl_2$. The mixture was incubated at 37° C. and the milk-clotting time was determined by visual observation, and the results are shown in FIG. 10.

Once again, all constructs excepting pCBΔPSI_2C and pCBΔPSIΔloop were able to clot skim milk (for these two constructs, milk-clotting activity was observed only after a 16 h incubation period), which likely reflects their low production efficiency.

TABLE VII

Milk-clotting activity of different cardosin B constructs

| Construct | Positive clone/ total clones | Milk Clotting time (lowest time) | Milk-Clotting (sample concentration, time) |
|---|---|---|---|
| pCBΔPSI | 10/10 | 40' | ✓ |
| pCBΔPSI_4G | 10/10 | 50' | ✓ |
| pCBΔPSI_6G | 10/10 | 75' | ✓ |
| pCBΔPSI_NQG | 9/10 | 40' | ✓ |
| pCBΔPSIΔLinker | 10/10 | 40' | ✓ |
| pCBΔPSI_2C | 9/10 | 16 h | ✓ |
| pCBΔPSIΔLoop | 9/10 | 16 h | ✓ |

Conclusions

Figure 11A:
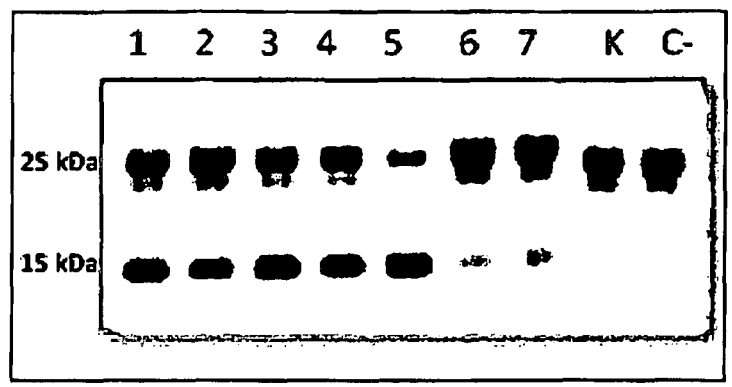
FIG. 11. Summary of cardosin B construct study—one clone of each construct was selected and both k-casein and western-blot experiments were repeated in order to obtain a summarized figure of this study.
Figure 11B:
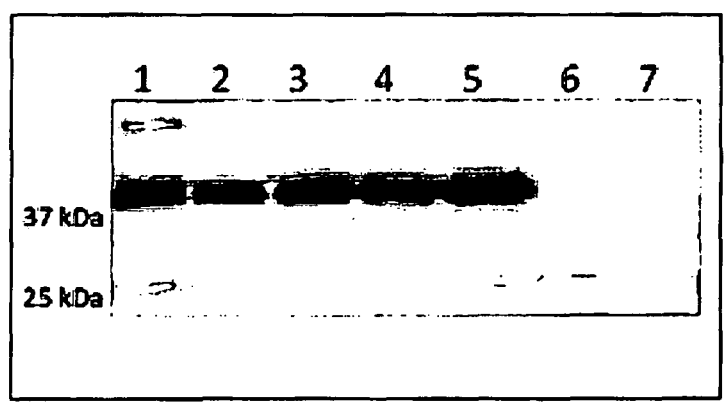

A summary of the results of this study are shown in FIG. 11, in which one clone of each construct was selected and both k-casein and western lot experiments were repeated. This study revealed that different constructs of cardosin B exhibit significant expression and secretion yields and good milk-clotting and caseinolytic activity, conditions that are required for cheese manufacturing. Moreover, it was possible to verify that the partial removal of PSI domain influence protein production without impairing caseinolytic activity.

REFERENCES

1 Vitale A & Hinz G, 2005. Trends in Plant Sci, 10(7): 316-323
2 Törmäkangas K et al, 2001. Plant Cell, 13: 2021-2032
3 Simões I & Faro C, 2004. Eur. J. Biochem. 271, 2067-2075
4 Törmökangas K et al, 2001. Plant Cell, 13: 2021-2032
5 Ramalho-Santos M et al, 1998. Eur J Biochem, 255: 133-138
6 Duarte A S, et al, 2005. Current Drug Disc Tech, 2: 37-44
7 PCT Patent publication No WO9507687
8 Patent publication No JP2000247907
9 US patent publication No US2003040047
10 Verissimo P et al (1996) Eur J Biochem. 235(3):762-8.
11 Verissimo P et al (1996) Eur J Biochem, 762-768
12 Chu T C, 1997. Medicine, 25:30-33
13 Smithard A et al, 2001. Br J Dermatol, 145:274-279
14 Pearl A et al, 1998. N Z Med J, 111:269-271
15 Cunliffe W J, 1998. J Cutan Med Surg, 2(suppl 3):7-13
16 Fowler J F et al, 2008. J Am Acad Dermatol, 59(5):772-80
17 Horn E J et al, 2007. J Am Acad Dermatol, 57(6):963-71
18 Egas C et al, 2000. J. Biol. Chem, 275, 38190-38196
19 Claverie-Martin et al, 2007. Industrial Enzymes 207-219

The invention claimed is:

1. A method for producing a plant aspartic protease, wherein the plant aspartic protease is a modified cardosin, the method comprising expressing, in a yeast cell or a fungal cell, a nucleic acid encoding
   (i) a polypeptide of SEQ ID NO: 1, or SEQ ID NO: 2; or
   (ii) a polypeptide having at least 95% sequence identity to SEQ ID NO: 1, or SEQ ID NO: 2, wherein the polypeptide encoded lacks a functional plant specific insert (PSI) domain.

2. The method of claim 1, wherein modified cardosin is secreted from the cell, the method further comprising collecting modified cardosin secreted from the cell.

3. The method of claim 1 wherein the modified cardosin is expressed from a vector contained in the cell, or wherein the modified cardosin is expressed from the genome of the cell.

4. The method of claim 1 wherein the yeast is from the genus *Kluyveromyces*.

5. The method of claim 1 (ii) wherein the PSI domain is wholly or partially replaced by a linker peptide.

6. The method of claim 1 wherein the modified cardosin does not have sequence AEAA or AEAV at the C-terminus.

7. The method of claim 3 wherein the vector is a yeast expression vector.

* * * * *

SEQUENCE LISTING

```
<160> NUMBER OF SEQ ID NOS: 20

<210> SEQ ID NO 1
<211> LENGTH: 383
<212> TYPE: PRT
<213> ORGANISM: Artificial sequence
<220> FEATURE:
<223> OTHER INFORMATION: Synthetic construct

<400> SEQUENCE: 1

Met Val Ser Asn Gly Gly Leu Leu Arg Val Gly Leu Lys Lys Arg Lys
1               5                   10                  15

Val Asp Arg Leu Asp Gln Leu Arg Ala His Gly Val His Met Leu Gly
            20                  25                  30

Asn Ala Arg Lys Asp Phe Gly Phe Arg Arg Thr Leu Arg Asp Ser Gly
        35                  40                  45

Ser Gly Ile Val Ala Leu Thr Asn Asp Arg Asp Thr Ala Tyr Tyr Gly
    50                  55                  60

Glu Ile Gly Ile Gly Thr Pro Pro Gln Asn Phe Ala Val Ile Phe Asp
65                  70                  75                  80

Thr Gly Ser Ser Asp Leu Trp Val Pro Ser Thr Lys Cys Asp Thr Ser
            85                  90                  95

Leu Ala Cys Val Ile His Pro Arg Tyr Asp Ser Gly Asp Ser Ser Thr
            100                 105                 110

Tyr Lys Gly Asn Gly Thr Thr Ala Ser Ile Gln Tyr Gly Thr Gly Ala
        115                 120                 125

Ile Val Gly Phe Tyr Ser Gln Asp Ser Val Glu Val Gly Asp Leu Val
    130                 135                 140

Val Glu His Gln Asp Phe Ile Glu Thr Thr Glu Glu Asp Asp Thr Val
```

```
                145                 150                 155                 160
        Phe Leu Lys Ser Glu Phe Asp Gly Ile Leu Gly Leu Gly Phe Gln Glu
                        165                 170                 175

Ile Ser Ala Gly Lys Ala Val Pro Val Trp Tyr Asn Met Val Asn Gln
                        180                 185                 190

Gly Leu Val Glu Glu Ala Val Phe Ser Phe Trp Leu Asn Arg Asn Val
                        195                 200                 205

Asp Glu Glu Gly Gly Glu Leu Val Phe Gly Val Asp Pro Asn
                        210                 215                 220

His Phe Arg Gly Asn His Thr Tyr Val Pro Val Thr Arg Lys Gly Tyr
        225                 230                 235                 240

Trp Gln Phe Glu Met Gly Asp Val Leu Ile Gly Asp Lys Ser Ser Gly
                        245                 250                 255

Phe Cys Ala Gly Gly Cys Ala Ala Ile Ala Asp Ser Gly Thr Ser Phe
                        260                 265                 270

Phe Ala Gly Pro Thr Ala Ile Ile Thr Gln Ile Asn Gln Ala Ile Gly
                        275                 280                 285

Ala Lys Gly Gly Gly Ser Ala Glu Ser Ile Val Asp Cys Asn Gly
                        290                 295                 300

Ile Ser Ser Met Pro Asn Ile Ala Phe Thr Ile Gly Ser Lys Leu Phe
        305                 310                 315                 320

Glu Val Thr Pro Glu Gln Tyr Ile Tyr Lys Val Gly Glu Gly Glu Ala
                        325                 330                 335

Ala Thr Cys Ile Ser Gly Phe Thr Ala Leu Asp Ile Met Ser Pro Gln
                        340                 345                 350

Gly Pro Ile Trp Ile Leu Gly Asp Met Phe Met Gly Pro Tyr His Thr
                        355                 360                 365

Val Phe Asp Tyr Gly Lys Leu Arg Val Gly Phe Ala Glu Ala Val
                        370                 375                 380

<210> SEQ ID NO 2
<211> LENGTH: 377
<212> TYPE: PRT
<213> ORGANISM: Artificial sequence
<220> FEATURE:
<223> OTHER INFORMATION: Synthetic construct

<400> SEQUENCE: 2

Met Ser Asp Asp Gly Leu Ile Arg Ile Gly Leu Lys Lys Arg Lys Val
1               5                   10                  15

Asp Arg Ile Asp Gln Leu Arg Gly Arg Arg Ala Leu Met Glu Gly Asn
                20                  25                  30

Ala Arg Lys Asp Phe Gly Phe Arg Gly Thr Val Arg Asp Ser Gly Ser
                35                  40                  45

Ala Val Val Ala Leu Thr Asn Asp Arg Asp Thr Ser Tyr Phe Gly Glu
        50                  55                  60

Ile Gly Ile Gly Thr Pro Pro Gln Lys Phe Thr Val Ile Phe Asp Thr
65                  70                  75                  80

Gly Ser Ser Val Leu Trp Val Pro Ser Ser Lys Cys Ile Asn Ser Lys
                85                  90                  95

Ala Cys Arg Ala His Ser Met Tyr Glu Ser Ser Asp Ser Thr Tyr
                100                 105                 110

Lys Glu Asn Gly Thr Ser Gly Ala Ile Ile Tyr Gly Thr Gly Ser Ile
                115                 120                 125

Thr Gly Phe Phe Ser Gln Asp Ser Val Thr Ile Gly Asp Leu Val Val
```

```
                    130                 135                 140
Lys Glu Gln Asp Phe Ile Glu Ala Thr Asp Glu Ala Asp Asn Val Phe
145                 150                 155                 160

Leu His Arg Leu Phe Asp Gly Ile Leu Gly Leu Ser Phe Gln Thr Ile
                    165                 170                 175

Ser Val Pro Val Trp Tyr Asn Met Val Asn Gln Gly Leu Val Lys Glu
                180                 185                 190

Arg Arg Phe Ser Phe Trp Leu Asn Arg Asn Val Asp Glu Glu Glu Gly
                    195                 200                 205

Gly Glu Leu Val Phe Gly Gly Leu Asp Pro Asn His Phe Arg Gly Asp
                210                 215                 220

His Thr Tyr Val Pro Val Thr Tyr Gln Tyr Tyr Trp Gln Phe Gly Ile
225                 230                 235                 240

Gly Asp Val Leu Ile Gly Asp Lys Ser Thr Gly Phe Cys Ala Pro Gly
                    245                 250                 255

Cys Gln Ala Phe Ala Asp Ser Gly Thr Ser Leu Leu Ser Gly Pro Thr
                260                 265                 270

Ala Ile Val Thr Gln Ile Asn His Ala Ile Gly Ala Asn Gly Gly Gly
                    275                 280                 285

Gly Ser Glu Glu Leu Gln Val Asp Cys Asn Thr Leu Ser Ser Met Pro
                290                 295                 300

Asn Val Ser Phe Thr Ile Gly Gly Lys Lys Phe Gly Leu Thr Pro Glu
305                 310                 315                 320

Gln Tyr Ile Leu Lys Val Gly Lys Gly Glu Ala Thr Gln Cys Ile Ser
                    325                 330                 335

Gly Phe Thr Ala Met Asp Ala Thr Leu Leu Gly Pro Leu Trp Ile Leu
                340                 345                 350

Gly Asp Val Phe Met Arg Pro Tyr His Thr Val Phe Asp Tyr Gly Asn
                    355                 360                 365

Leu Leu Val Gly Phe Ala Glu Ala
                370                 375

<210> SEQ ID NO 3
<211> LENGTH: 106
<212> TYPE: PRT
<213> ORGANISM: Artificial sequence
<220> FEATURE:
<223> OTHER INFORMATION: Synthetic construct

<400> SEQUENCE: 3

Val Met Asn Gln Gln Cys Lys Thr Val Val Ser Arg Tyr Gly Arg Asp
1               5                   10                  15

Ile Ile Glu Met Leu Arg Ser Lys Ile Gln Pro Asp Lys Ile Cys Ser
                20                  25                  30

His Met Lys Leu Cys Thr Phe Asp Gly Ala Arg Asp Val Ser Ser Ile
                35                  40                  45

Ile Glu Ser Val Val Asp Lys Asn Asn Asp Lys Ser Ser Gly Gly Ile
            50                  55                  60

His Asp Glu Met Cys Thr Phe Cys Glu Met Ala Val Val Trp Met Gln
65                  70                  75                  80

Asn Glu Ile Lys Gln Ser Glu Thr Glu Asp Asn Ile Ile Asn Tyr Ala
                85                  90                  95

Asn Glu Leu Cys Glu His Leu Ser Thr Ser
                100                 105
```

<210> SEQ ID NO 4
<211> LENGTH: 103
<212> TYPE: PRT
<213> ORGANISM: Artificial sequence
<220> FEATURE:
<223> OTHER INFORMATION: Synthetic construct

<400> SEQUENCE: 4

Val Leu Asn Gln Gln Cys Lys Thr Leu Val Gly Gln Tyr Gly Lys Asn
1               5                   10                  15

Met Val Gln Met Leu Thr Ser Glu Val Gln Pro Asp Lys Ile Cys Ser
            20                  25                  30

His Met Lys Leu Cys Thr Phe Asp Gly Ala His Asp Val Arg Ser Met
        35                  40                  45

Ile Glu Ser Val Val Asp Lys Asn Asn Asp Lys Ser Ser Gly Gly Glu
50                  55                  60

Ile Cys Thr Phe Cys Glu Met Ala Leu Val Arg Met Gln Asn Glu Ile
65                  70                  75                  80

Lys Arg Asn Glu Thr Glu Asp Asn Ile Ile Asn His Val Asn Glu Val
                85                  90                  95

Cys Asp Gln Leu Pro Thr Ser
            100

<210> SEQ ID NO 5
<211> LENGTH: 483
<212> TYPE: PRT
<213> ORGANISM: Cynara cardunculus

<400> SEQUENCE: 5

Met Val Ser Asn Gly Gly Leu Leu Arg Val Gly Leu Lys Lys Arg Lys
1               5                   10                  15

Val Asp Arg Leu Asp Gln Leu Arg Ala His Gly Val His Met Leu Gly
            20                  25                  30

Asn Ala Arg Lys Asp Phe Gly Phe Arg Arg Thr Leu Arg Asp Ser Gly
        35                  40                  45

Ser Gly Ile Val Ala Leu Thr Asn Asp Arg Asp Thr Ala Tyr Tyr Gly
    50                  55                  60

Glu Ile Gly Ile Gly Thr Pro Pro Gln Asn Phe Ala Val Ile Phe Asp
65                  70                  75                  80

Thr Gly Ser Ser Asp Leu Trp Val Pro Ser Thr Lys Cys Asp Thr Ser
                85                  90                  95

Leu Ala Cys Val Ile His Pro Arg Tyr Asp Ser Gly Asp Ser Ser Thr
            100                 105                 110

Tyr Lys Gly Asn Gly Thr Thr Ala Ser Ile Gln Tyr Gly Thr Gly Ala
        115                 120                 125

Ile Val Gly Phe Tyr Ser Gln Asp Ser Val Glu Val Gly Asp Leu Val
    130                 135                 140

Val Glu His Gln Asp Phe Ile Glu Thr Thr Glu Glu Asp Asp Thr Val
145                 150                 155                 160

Phe Leu Lys Ser Glu Phe Asp Gly Ile Leu Gly Leu Gly Phe Gln Glu
                165                 170                 175

Ile Ser Ala Gly Lys Ala Val Pro Val Trp Tyr Asn Met Val Asn Gln
            180                 185                 190

Gly Leu Val Glu Glu Ala Val Phe Ser Phe Trp Leu Asn Arg Asn Val
        195                 200                 205

Asp Glu Glu Glu Gly Gly Glu Leu Val Phe Gly Gly Val Asp Pro Asn
    210                 215                 220

His Phe Arg Gly Asn His Thr Tyr Val Pro Val Thr Arg Lys Gly Tyr
225                 230                 235                 240

Trp Gln Phe Glu Met Gly Asp Val Leu Ile Gly Asp Lys Ser Ser Gly
            245                 250                 255

Phe Cys Ala Gly Gly Cys Ala Ala Ile Ala Asp Ser Gly Thr Ser Phe
            260                 265                 270

Phe Ala Gly Pro Thr Ala Ile Ile Thr Gln Ile Asn Gln Ala Ile Gly
            275                 280                 285

Ala Lys Gly Val Leu Asn Gln Gln Cys Lys Thr Leu Val Gly Gln Tyr
            290                 295                 300

Gly Lys Asn Met Val Gln Met Leu Thr Ser Glu Val Gln Pro Asp Lys
305                 310                 315                 320

Ile Cys Ser His Met Lys Leu Cys Thr Phe Asp Gly Ala His Asp Val
                325                 330                 335

Arg Ser Met Ile Glu Ser Val Val Asp Lys Asn Asn Asp Lys Ser Ser
                340                 345                 350

Gly Gly Glu Ile Cys Thr Phe Cys Glu Met Ala Leu Val Arg Met Gln
            355                 360                 365

Asn Glu Ile Lys Arg Asn Glu Thr Glu Asp Asn Ile Ile Asn His Val
    370                 375                 380

Asn Glu Val Cys Asp Gln Leu Pro Thr Ser Ser Ala Glu Ser Met Val
385                 390                 395                 400

Asp Cys Asn Gly Ile Ser Ser Met Pro Asn Ile Ala Phe Thr Ile Gly
                405                 410                 415

Ser Lys Leu Phe Glu Val Thr Pro Glu Gln Tyr Ile Tyr Lys Val Gly
            420                 425                 430

Glu Gly Glu Ala Ala Thr Cys Ile Ser Gly Phe Thr Ala Leu Asp Ile
            435                 440                 445

Met Ser Pro Gln Gly Pro Ile Trp Ile Leu Gly Asp Met Phe Met Gly
    450                 455                 460

Pro Tyr His Thr Val Phe Asp Tyr Gly Lys Leu Arg Val Gly Phe Ala
465                 470                 475                 480

Glu Ala Val

<210> SEQ ID NO 6
<211> LENGTH: 480
<212> TYPE: PRT
<213> ORGANISM: Cynara cardunculus

<400> SEQUENCE: 6

Met Ser Asp Asp Gly Leu Ile Arg Ile Gly Leu Lys Lys Arg Lys Val
1               5                   10                  15

Asp Arg Ile Asp Gln Leu Arg Gly Arg Arg Ala Leu Met Glu Gly Asn
            20                  25                  30

Ala Arg Lys Asp Phe Gly Phe Arg Gly Thr Val Arg Asp Ser Gly Ser
        35                  40                  45

Ala Val Val Ala Leu Thr Asn Asp Arg Asp Thr Ser Tyr Phe Gly Glu
    50                  55                  60

Ile Gly Ile Gly Thr Pro Pro Gln Lys Phe Thr Val Ile Phe Asp Thr
65                  70                  75                  80

Gly Ser Ser Val Leu Trp Val Pro Ser Ser Lys Cys Ile Asn Ser Lys
                85                  90                  95

Ala Cys Arg Ala His Ser Met Tyr Glu Ser Ser Asp Ser Ser Thr Tyr
            100                 105                 110

-continued

Lys Glu Asn Gly Thr Ser Gly Ala Ile Ile Tyr Gly Thr Gly Ser Ile
         115                 120                 125

Thr Gly Phe Phe Ser Gln Asp Ser Val Thr Ile Gly Asp Leu Val Val
    130                 135                 140

Lys Glu Gln Asp Phe Ile Glu Ala Thr Asp Glu Ala Asp Asn Val Phe
145                 150                 155                 160

Leu His Arg Leu Phe Asp Gly Ile Leu Gly Leu Ser Phe Gln Thr Ile
                165                 170                 175

Ser Val Pro Val Trp Tyr Asn Met Val Asn Gln Gly Leu Val Lys Glu
            180                 185                 190

Arg Arg Phe Ser Phe Trp Leu Asn Arg Asn Val Asp Glu Glu Glu Gly
            195                 200                 205

Gly Glu Leu Val Phe Gly Gly Leu Asp Pro Asn His Phe Arg Gly Asp
        210                 215                 220

His Thr Tyr Val Pro Val Thr Tyr Gln Tyr Tyr Trp Gln Phe Gly Ile
225                 230                 235                 240

Gly Asp Val Leu Ile Gly Asp Lys Ser Thr Gly Phe Cys Ala Pro Gly
                245                 250                 255

Cys Gln Ala Phe Ala Asp Ser Gly Thr Ser Leu Leu Ser Gly Pro Thr
            260                 265                 270

Ala Ile Val Thr Gln Ile Asn His Ala Ile Gly Ala Asn Gly Val Met
        275                 280                 285

Asn Gln Gln Cys Lys Thr Val Val Ser Arg Tyr Gly Arg Asp Ile Ile
        290                 295                 300

Glu Met Leu Arg Ser Lys Ile Gln Pro Asp Lys Ile Cys Ser His Met
305                 310                 315                 320

Lys Leu Cys Thr Phe Asp Gly Ala Arg Asp Val Ser Ser Ile Ile Glu
                325                 330                 335

Ser Val Val Asp Lys Asn Asn Asp Lys Ser Ser Gly Gly Ile His Asp
            340                 345                 350

Glu Met Cys Thr Phe Cys Glu Met Ala Val Val Trp Met Gln Asn Glu
        355                 360                 365

Ile Lys Gln Ser Glu Thr Glu Asp Asn Ile Ile Asn Tyr Ala Asn Glu
        370                 375                 380

Leu Cys Glu His Leu Ser Thr Ser Ser Glu Glu Leu Gln Val Asp Cys
385                 390                 395                 400

Asn Thr Leu Ser Ser Met Pro Asn Val Ser Phe Thr Ile Gly Gly Lys
                405                 410                 415

Lys Phe Gly Leu Thr Pro Glu Gln Tyr Ile Leu Lys Val Gly Lys Gly
            420                 425                 430

Glu Ala Thr Gln Cys Ile Ser Gly Phe Thr Ala Met Asp Ala Thr Leu
        435                 440                 445

Leu Gly Pro Leu Trp Ile Leu Gly Asp Val Phe Met Arg Pro Tyr His
    450                 455                 460

Thr Val Phe Asp Tyr Gly Asn Leu Leu Val Gly Phe Ala Glu Ala Ala
465                 470                 475                 480

<210> SEQ ID NO 7
<211> LENGTH: 37
<212> TYPE: DNA
<213> ORGANISM: Artificial sequence
<220> FEATURE:
<223> OTHER INFORMATION: Synthetic construct

<400> SEQUENCE: 7

-continued ctcgagaaaa gaatggtctc caacggcgga ttgcttc                                37

<210> SEQ ID NO 8
<211> LENGTH: 37
<212> TYPE: DNA
<213> ORGANISM: Artificial sequence
<220> FEATURE:
<223> OTHER INFORMATION: Synthetic construct

<400> SEQUENCE: 8
gtcgactcaa actgcttctg caaatcccac tcgtaac                                37

<210> SEQ ID NO 9
<211> LENGTH: 4
<212> TYPE: PRT
<213> ORGANISM: Cynara cardunculus

<400> SEQUENCE: 9

Ala Glu Ala Ala
1

<210> SEQ ID NO 10
<211> LENGTH: 4
<212> TYPE: PRT
<213> ORGANISM: Cynara cardunculus

<400> SEQUENCE: 10

Ala Glu Ala Val
1

<210> SEQ ID NO 11
<211> LENGTH: 504
<212> TYPE: PRT
<213> ORGANISM: Cynara cardunculus

<400> SEQUENCE: 11

```
Met Gly Thr Ser Ile Lys Ala Asn Val Leu Ala Leu Phe Leu Phe Tyr
1               5                   10                  15

Leu Leu Ser Pro Thr Val Phe Ser Val Ser Asp Asp Gly Leu Ile Arg
            20                  25                  30

Ile Gly Leu Lys Lys Arg Lys Val Asp Arg Ile Asp Gln Leu Arg Gly
        35                  40                  45

Arg Arg Ala Leu Met Glu Gly Asn Ala Arg Lys Asp Phe Gly Phe Arg
    50                  55                  60

Gly Thr Val Arg Asp Ser Gly Ser Ala Val Val Ala Leu Thr Asn Asp
65                  70                  75                  80

Arg Asp Thr Ser Tyr Phe Gly Glu Ile Gly Ile Gly Thr Pro Pro Gln
                85                  90                  95

Lys Phe Thr Val Ile Phe Asp Thr Gly Ser Ser Val Leu Trp Val Pro
            100                 105                 110

Ser Ser Lys Cys Ile Asn Ser Lys Ala Cys Arg Ala His Ser Met Tyr
        115                 120                 125

Glu Ser Ser Asp Ser Ser Thr Tyr Lys Glu Asn Gly Thr Phe Gly Ala
    130                 135                 140

Ile Ile Tyr Gly Thr Gly Ser Ile Thr Gly Phe Phe Ser Gln Asp Ser
145                 150                 155                 160

Val Thr Ile Gly Asp Leu Val Val Lys Glu Gln Asp Phe Ile Glu Ala
                165                 170                 175

Thr Asp Glu Ala Asp Asn Val Phe Leu His Arg Leu Phe Asp Gly Ile
```

```
                    180                 185                 190
Leu Gly Leu Ser Phe Gln Thr Ile Ser Val Pro Val Trp Tyr Asn Met
            195                 200                 205

Leu Asn Gln Gly Leu Val Lys Glu Arg Arg Phe Ser Phe Trp Leu Asn
        210                 215                 220

Arg Asn Val Asp Glu Glu Gly Gly Glu Leu Val Phe Gly Gly Leu
225                 230                 235                 240

Asp Pro Asn His Phe Arg Gly Asp His Thr Tyr Val Pro Val Thr Tyr
                245                 250                 255

Gln Tyr Tyr Trp Gln Phe Gly Ile Gly Asp Val Leu Ile Gly Asp Lys
            260                 265                 270

Ser Thr Gly Phe Cys Ala Pro Gly Cys Gln Ala Phe Ala Asp Ser Gly
        275                 280                 285

Thr Ser Leu Leu Ser Gly Pro Thr Ala Ile Val Thr Gln Ile Asn His
        290                 295                 300

Ala Ile Gly Ala Asn Gly Val Met Asn Gln Gln Cys Lys Thr Val Val
305                 310                 315                 320

Ser Arg Tyr Gly Arg Asp Ile Ile Glu Met Leu Arg Ser Lys Ile Gln
                325                 330                 335

Pro Asp Lys Ile Cys Ser His Met Lys Leu Cys Thr Phe Asp Gly Ala
            340                 345                 350

Arg Asp Val Ser Ser Ile Ile Glu Ser Val Val Asp Lys Asn Asn Asp
        355                 360                 365

Lys Ser Ser Gly Gly Ile His Asp Glu Met Cys Thr Phe Cys Glu Met
        370                 375                 380

Ala Val Val Trp Met Gln Asn Glu Ile Lys Gln Ser Glu Thr Glu Asp
385                 390                 395                 400

Asn Ile Ile Asn Tyr Ala Asn Glu Leu Cys Glu His Leu Ser Thr Ser
                405                 410                 415

Ser Glu Glu Leu Gln Val Asp Cys Asn Thr Leu Ser Ser Met Pro Asn
            420                 425                 430

Val Ser Phe Thr Ile Gly Gly Lys Lys Phe Gly Leu Thr Pro Glu Gln
        435                 440                 445

Tyr Ile Leu Lys Val Gly Lys Gly Glu Ala Thr Gln Cys Ile Ser Gly
        450                 455                 460

Phe Thr Ala Met Asp Ala Thr Leu Leu Gly Pro Leu Trp Ile Leu Gly
465                 470                 475                 480

Asp Val Phe Met Arg Pro Tyr His Thr Val Phe Asp Tyr Gly Asn Leu
                485                 490                 495

Leu Val Gly Phe Ala Glu Ala Ala
            500

<210> SEQ ID NO 12
<211> LENGTH: 506
<212> TYPE: PRT
<213> ORGANISM: Cynara cardunculus

<400> SEQUENCE: 12

Met Gly Thr Pro Ile Lys Ala Ser Leu Leu Ala Leu Phe Leu Phe Phe
1               5                   10                  15

Leu Leu Ser Pro Thr Ala Phe Ser Val Ser Asn Gly Gly Leu Leu Arg
            20                  25                  30

Val Gly Leu Lys Lys Arg Lys Val Asp Arg Leu Asp Gln Leu Arg Ala
        35                  40                  45
```

-continued

```
His Gly Val His Met Leu Gly Asn Ala Arg Lys Asp Phe Gly Phe Arg
     50                  55                  60

Arg Thr Leu Ser Asp Ser Gly Ser Gly Ile Val Ala Leu Thr Asn Asp
 65                  70                  75                  80

Arg Asp Thr Ala Tyr Tyr Gly Glu Ile Gly Ile Gly Thr Pro Pro Gln
                     85                  90                  95

Asn Phe Ala Val Ile Phe Asp Thr Gly Ser Ser Asp Leu Trp Val Pro
                 100                 105                 110

Ser Thr Lys Cys Asp Thr Ser Leu Ala Cys Val Ile His Pro Arg Tyr
             115                 120                 125

Asp Ser Gly Asp Ser Ser Thr Tyr Lys Gly Asn Gly Thr Thr Ala Ser
         130                 135                 140

Ile Gln Tyr Gly Thr Gly Ala Ile Val Gly Phe Tyr Ser Gln Asp Ser
145                 150                 155                 160

Val Glu Val Gly Asp Leu Val Val Glu His Gln Asp Phe Ile Glu Thr
                 165                 170                 175

Thr Glu Glu Asp Asp Thr Val Phe Leu Lys Ser Glu Phe Asp Gly Ile
             180                 185                 190

Leu Gly Leu Gly Phe Gln Glu Ile Ser Ala Gly Lys Ala Val Pro Val
         195                 200                 205

Trp Tyr Asn Met Val Asn Gln Gly Leu Val Glu Glu Ala Val Phe Ser
210                 215                 220

Phe Trp Leu Asn Arg Asn Val Asp Glu Glu Glu Gly Gly Glu Leu Val
225                 230                 235                 240

Phe Gly Gly Val Asp Pro Asn His Phe Arg Gly Asn His Thr Tyr Val
                 245                 250                 255

Pro Val Thr Arg Lys Gly Tyr Trp Gln Phe Glu Met Gly Asp Val Leu
             260                 265                 270

Ile Gly Asp Lys Ser Ser Gly Phe Cys Ala Gly Gly Cys Ala Ala Ile
         275                 280                 285

Ala Asp Ser Gly Thr Ser Phe Phe Ala Gly Pro Thr Ala Ile Ile Thr
290                 295                 300

Gln Ile Asn Gln Ala Ile Gly Ala Lys Gly Val Leu Asn Gln Gln Cys
305                 310                 315                 320

Lys Thr Leu Val Gly Gln Tyr Gly Lys Asn Met Ile Gln Met Leu Thr
                 325                 330                 335

Ser Glu Val Gln Pro Asp Lys Ile Cys Ser His Met Lys Leu Cys Thr
             340                 345                 350

Phe Asp Gly Ala His Asp Val Arg Ser Met Ile Glu Ser Val Val Asp
         355                 360                 365

Lys Asn Asn Asp Lys Ser Ser Gly Gly Glu Ile Cys Thr Phe Cys Glu
370                 375                 380

Met Ala Leu Val Arg Met Gln Asn Glu Ile Lys Arg Asn Glu Thr Glu
385                 390                 395                 400

Asp Asn Ile Ile Asn His Val Asn Glu Val Cys Asp Gln Leu Pro Thr
                 405                 410                 415

Ser Ser Ala Glu Ser Ile Val Asp Cys Asn Gly Ile Ser Ser Met Pro
             420                 425                 430

Asn Ile Ala Phe Thr Ile Gly Ser Lys Leu Phe Glu Val Thr Pro Glu
         435                 440                 445

Gln Tyr Ile Tyr Lys Val Gly Glu Gly Glu Ala Ala Thr Cys Ile Ser
450                 455                 460

Gly Phe Thr Ala Leu Asp Ile Met Ser Pro Gln Gly Pro Ile Trp Ile
```

```
                465                 470                 475                 480
Leu Gly Asp Met Phe Met Gly Pro Tyr His Thr Val Phe Asp Tyr Gly
                    485                 490                 495
Lys Leu Arg Val Gly Phe Ala Glu Ala Val
                500                 505

<210> SEQ ID NO 13
<211> LENGTH: 120
<212> TYPE: PRT
<213> ORGANISM: Artificial sequence
<220> FEATURE:
<223> OTHER INFORMATION: Synthetic construct

<400> SEQUENCE: 13

Asn Gln Ala Ile Gly Ala Lys Gly Val Leu Asn Gln Gln Cys Lys Thr
1               5                   10                  15
Leu Val Gly Gln Tyr Gly Lys Asn Met Val Gln Met Leu Thr Ser Glu
                20                  25                  30
Val Gln Pro Asp Lys Ile Cys Ser His Met Lys Leu Cys Thr Phe Asp
            35                  40                  45
Gly Ala His Asp Val Arg Ser Met Ile Glu Ser Val Val Asp Lys Asn
        50                  55                  60
Asn Asp Lys Ser Ser Gly Gly Glu Ile Cys Thr Phe Cys Glu Met Ala
65                  70                  75                  80
Leu Val Arg Met Gln Asn Glu Ile Lys Arg Asn Glu Thr Glu Asp Asn
                85                  90                  95
Ile Ile Asn His Val Asn Glu Val Cys Asp Gln Leu Pro Thr Ser Ser
            100                 105                 110
Ala Glu Ser Ile Val Asp Cys Asn
        115                 120

<210> SEQ ID NO 14
<211> LENGTH: 20
<212> TYPE: PRT
<213> ORGANISM: Artificial sequence
<220> FEATURE:
<223> OTHER INFORMATION: Synthetic construct

<400> SEQUENCE: 14

Asn Gln Ala Ile Gly Ala Lys Gly Gly Gly Gly Ser Ala Glu Ser Ile
1               5                   10                  15
Val Asp Cys Asn
            20

<210> SEQ ID NO 15
<211> LENGTH: 21
<212> TYPE: PRT
<213> ORGANISM: Artificial sequence
<220> FEATURE:
<223> OTHER INFORMATION: Synthetic construct

<400> SEQUENCE: 15

Asn Gln Ala Ile Gly Ala Lys Gly Gly Gly Gly Gly Ser Ala Glu Ser
1               5                   10                  15
Ile Val Asp Cys Asn
            20

<210> SEQ ID NO 16
<211> LENGTH: 23
<212> TYPE: PRT
<213> ORGANISM: Artificial sequence
```

```
<220> FEATURE:
<223> OTHER INFORMATION: Synthetic construct

<400> SEQUENCE: 16

Asn Gln Ala Ile Gly Ala Lys Gly Gly Gly Gly Gly Gly Ser Ala
1               5                   10                  15

Glu Ser Ile Val Asp Cys Asn
            20

<210> SEQ ID NO 17
<211> LENGTH: 20
<212> TYPE: PRT
<213> ORGANISM: Artificial sequence
<220> FEATURE:
<223> OTHER INFORMATION: Synthetic construct

<400> SEQUENCE: 17

Asn Gln Ala Ile Gly Ala Lys Gly Asn Gln Gly Ser Ala Glu Ser Ile
1               5                   10                  15

Val Asp Cys Asn
            20

<210> SEQ ID NO 18
<211> LENGTH: 17
<212> TYPE: PRT
<213> ORGANISM: Artificial sequence
<220> FEATURE:
<223> OTHER INFORMATION: Synthetic construct

<400> SEQUENCE: 18

Asn Gln Ala Ile Gly Ala Lys Gly Ser Ala Glu Ser Ile Val Asp Cys
1               5                   10                  15

Asn

<210> SEQ ID NO 19
<211> LENGTH: 50
<212> TYPE: PRT
<213> ORGANISM: Artificial sequence
<220> FEATURE:
<223> OTHER INFORMATION: Synthetic construct

<400> SEQUENCE: 19

Asn Gln Ala Ile Gly Ala Lys Gly Val Leu Asn Gln Gln Cys Lys Thr
1               5                   10                  15

Leu Val Gly Gln Tyr Glu Thr Glu Asp Asn Ile Ile Asn His Val Asn
                20                  25                  30

Glu Val Cys Asp Gln Leu Pro Thr Ser Ser Ala Glu Ser Ile Val Asp
            35                  40                  45

Cys Asn
    50

<210> SEQ ID NO 20
<211> LENGTH: 101
<212> TYPE: PRT
<213> ORGANISM: Artificial sequence
<220> FEATURE:
<223> OTHER INFORMATION: Synthetic construct

<400> SEQUENCE: 20

Asn Gln Ala Ile Gly Ala Lys Gly Val Leu Asn Gln Gln Cys Lys Thr
1               5                   10                  15

Leu Val Gly Gln Tyr Gly Lys Asn Met Val Gln Met Leu Thr Ser Glu
                20                  25                  30
```

```
Val Gln Pro Asp Lys Ile Cys Ser His Met Lys Leu Cys Thr Phe Asp
        35              40              45

Gly Ala Gly Gly Glu Ile Cys Thr Phe Cys Glu Met Ala Leu Val Arg
        50              55              60

Met Gln Asn Glu Ile Lys Arg Asn Glu Thr Glu Asp Asn Ile Ile Asn
 65              70              75              80

His Val Asn Glu Val Cys Asp Gln Leu Pro Thr Ser Ser Ala Glu Ser
            85              90              95

Ile Val Asp Cys Asn
            100
```